(12) United States Patent
Jayaraman

(10) Patent No.: US 12,232,737 B2
(45) Date of Patent: Feb. 25, 2025

(54) OCCLUDING ANATOMICAL STRUCTURES

(71) Applicant: Eclipse Medical Limited, Dublin (IE)

(72) Inventor: Swaminathan Jayaraman, Pleasanton, CA (US)

(73) Assignee: Eclipse Medical Limited, Dublin (IE)

( * ) Notice: Subject to any disclaimer, the term of this patent is extended or adjusted under 35 U.S.C. 154(b) by 399 days.

(21) Appl. No.: 17/677,316

(22) Filed: Feb. 22, 2022

(65) Prior Publication Data
US 2022/0175392 A1    Jun. 9, 2022

Related U.S. Application Data

(63) Continuation-in-part of application No. 16/085,609, filed as application No. PCT/US2017/022986 on Mar. 17, 2017, now Pat. No. 11,253,261.
(Continued)

(51) Int. Cl.
*A61B 17/12* (2006.01)
*A61B 17/00* (2006.01)

(52) U.S. Cl.
CPC .. *A61B 17/12172* (2013.01); *A61B 17/12122* (2013.01); *A61B 2017/00526* (2013.01); *A61B 2017/00579* (2013.01); *A61B 2017/00597* (2013.01); *A61B 2017/00632* (2013.01); *A61B 2017/00867* (2013.01)

(58) Field of Classification Search
CPC .......... A61B 17/0057; A61B 17/12113; A61B 17/12122; A61B 17/12136; A61B 17/1214; A61B 17/12168; A61B 17/12172; A61B 2017/00526; A61B 2017/00575; A61B 2017/00592; A61B 2017/00606;
(Continued)

(56) References Cited

U.S. PATENT DOCUMENTS

| 4,034,642 A | 7/1977 | Iannucci |
| 4,202,718 A | 5/1980 | Mizutani et al. |

(Continued)

FOREIGN PATENT DOCUMENTS

| CN | 101795628 | 8/2010 |
| CN | 101795628 B | 8/2010 |

(Continued)

OTHER PUBLICATIONS

Npl1 First_OfficeAction dated Aug. 12, 2020; for Chinese Patent Application No. 2017800273068 npl2 The English Translation of the First Office Action.
(Continued)

*Primary Examiner* — Brooke Labranche
(74) *Attorney, Agent, or Firm* — Fleit Intellectual Property Law; Paul D. Bianco; Gary S. Winer

(57) ABSTRACT

An elongate resilient tube of a mesh of shape memory alloy is used to therapeutically occlude an opening in body tissue. The tube is compressible so that it can be delivered to the opening in the body within a catheter. The tube self-expands as it is released from the catheter to contiguously form, sequentially an outer perimeter structure and an inner perimeter structure disposed within the outer perimeter structure to conformingly engage an inner side of the outer perimeter structure, a plate shaped structure, and a flexible connector between them. J-shaped hooks extend from the perimeter structure to flexibly engage tissue of the body opening without piercing the tissue.

20 Claims, 11 Drawing Sheets

Related U.S. Application Data

(60) Provisional application No. 62/309,578, filed on Mar. 17, 2016.

(58) Field of Classification Search
CPC .. A61B 2017/00623; A61B 2017/1205; A61B 2017/12095
See application file for complete search history.

(56) References Cited

U.S. PATENT DOCUMENTS

| | | | |
|---|---|---|---|
| 4,372,191 | A | 2/1983 | Iannucci |
| 4,621,560 | A | 11/1986 | Brown |
| 4,729,278 | A | 3/1988 | Graeff |
| 4,753,149 | A | 6/1988 | Celani |
| 4,934,240 | A | 6/1990 | Culp, Sr. |
| 5,099,744 | A | 3/1992 | Hurst |
| 5,176,062 | A | 1/1993 | Maillefer |
| 5,301,596 | A | 4/1994 | Huey, Jr. |
| 5,361,674 | A | 11/1994 | Akiyama |
| 5,419,231 | A | 5/1995 | Earle, III |
| 5,476,027 | A | 12/1995 | Uchida |
| 5,562,725 | A | 10/1996 | Schmitt et al. |
| 5,787,784 | A | 8/1998 | Scherzinger |
| 5,913,959 | A | 6/1999 | Klien |
| 5,944,738 | A | 8/1999 | Amplatz et al. |
| 5,972,019 | A | 10/1999 | Engelson et al. |
| 5,974,938 | A | 11/1999 | Lloyd |
| 6,626,939 | B1 | 9/2003 | Burnside et al. |
| 6,679,152 | B1 | 1/2004 | Head |
| 6,786,898 | B2 | 9/2004 | Guenst |
| 6,932,837 | B2 | 8/2005 | Amplatz et al. |
| 7,093,527 | B2 | 8/2006 | Rapaport |
| 7,165,945 | B2 | 1/2007 | Kovalsky |
| 7,270,043 | B2 | 9/2007 | Presz |
| 7,275,471 | B2 | 10/2007 | Nishri |
| 7,311,031 | B2 | 12/2007 | McCullagh et al. |
| 7,500,345 | B2 | 3/2009 | Kish |
| 8,034,061 | B2 | 10/2011 | Amplatz et al. |
| 8,377,114 | B2 | 2/2013 | Khairkhahan et al. |
| 8,398,670 | B2 | 3/2013 | Amplatz et al. |
| 8,747,432 | B1 | 6/2014 | Janardhan et al. |
| 8,758,389 | B2 | 6/2014 | Glimsdale |
| 8,777,974 | B2 | 7/2014 | Amplatz et al. |
| 8,961,556 | B2 | 2/2015 | Amplatz et al. |
| 9,295,472 | B2 | 3/2016 | Ottma |
| 9,445,799 | B2 | 9/2016 | Amplatz et al. |
| 9,554,806 | B2 | 1/2017 | Larsen et al. |
| 9,795,387 | B2 | 10/2017 | Miles et al. |
| 9,826,980 | B2 | 11/2017 | Figulla et al. |
| 9,861,346 | B2 | 1/2018 | Callaghan |
| 9,877,710 | B2 | 1/2018 | Amplatz et al. |
| 2001/0000797 | A1 | 5/2001 | Mazzocchi |
| 2001/0012949 | A1 | 8/2001 | Forber |
| 2003/0028209 | A1 | 2/2003 | Teoh et al. |
| 2004/0024416 | A1 | 2/2004 | Yoddat et al. |
| 2004/0073300 | A1 | 4/2004 | Chouinard |
| 2005/0228434 | A1 | 10/2005 | Amplatz et al. |
| 2006/0113714 | A1 | 6/2006 | Giloh et al. |
| 2006/0116714 | A1 | 6/2006 | Sepetka |
| 2007/0221230 | A1 | 9/2007 | Thompson et al. |
| 2007/0225760 | A1 | 9/2007 | Moszner et al. |
| 2007/0265656 | A1 | 11/2007 | Amplatz et al. |
| 2007/0043391 | A1 | 12/2007 | Moszner et al. |
| 2008/0104827 | A1 | 5/2008 | Kish |
| 2009/0018562 | A1 | 1/2009 | Amplatz |
| 2009/0198315 | A1 | 8/2009 | Boudjemline |
| 2009/0306706 | A1 | 12/2009 | Osypka |
| 2010/0191319 | A1 | 7/2010 | Lilburn et al. |
| 2011/0152993 | A1 | 6/2011 | Marchand |
| 2012/0065667 | A1 | 3/2012 | Javois |
| 2013/0131717 | A1 | 5/2013 | Glimsdale |
| 2013/0296912 | A1 | 11/2013 | Ottma |
| 2019/0110796 | A1 | 4/2019 | Jayaraman |

FOREIGN PATENT DOCUMENTS

| | | |
|---|---|---|
| CN | 102149424 | 8/2011 |
| CN | 102149424 A | 8/2011 |
| CN | 102639181 | 8/2012 |
| CN | 102639181 A | 8/2012 |
| CN | 204133530 | 2/2015 |
| CN | 204133530 U | 2/2015 |
| EP | 341434 A3 | 11/1989 |
| EP | 1621148 B1 | 2/2006 |
| EP | 2263553 A1 | 12/2010 |
| EP | 2340077 | 7/2011 |
| EP | 2340077 A1 | 7/2011 |
| EP | 2623039 A1 | 8/2013 |
| EP | 2779910 | 9/2014 |
| EP | 2779910 A1 | 9/2014 |
| EP | 2340077 B1 | 11/2016 |
| JP | 2014519858 A | 8/2014 |
| JP | 2015504335 A | 2/2015 |
| WO | 02071977 A2 | 9/2002 |
| WO | 2006052322 A2 | 5/2006 |
| WO | 2008022327 A2 | 2/2008 |
| WO | 2008/025405 A1 | 3/2008 |
| WO | 2010/030485 A1 | 3/2010 |
| WO | 2012/124762 A1 | 10/2012 |
| WO | 2012/134762 A1 | 10/2012 |
| WO | 2012134762 | 10/2012 |
| WO | 2013/028579 A1 | 2/2013 |
| WO | 2013/074486 A1 | 5/2013 |
| WO | 2013074486 | 5/2013 |

OTHER PUBLICATIONS

Npl3 The English Translation of Search Report dated Sep. 8, 2020; for Chinese Patent Application No. 2017800273068.
Npl4 Office Action for Japanese Patent Application No. 2018-568178, npl5 and English Translation of Office Action, date of dispatch Feb. 24, 2021.
Npl6 Second Office Action for CN Patent Application No. 2017800273068, dated Mar. 3, 2021, npl7 and English Translation of Office Action, dated Mar. 3, 2021.
Npl8 Notice Allowance English translation dated Jul. 29, 2021; for Japanese Patent Application No. 2018-568178.
European Search Report and Opinion for EP Patent Application No. 17767639.2, dated Sep. 19, 2019.
Ole De Backer et al., State-of-the-art Pre-Clinical Testing of the Omega TM Left Atrial Appendage Occluder; Medtronic, Wiley Periodicals 2020.
Ben Wilkins et al., First in Human Results of the Omega Left Atrial Appendage Occluder for Patients with Non-Valvular Atrial Febrillation; JAA, Euro Intervention; 2020.
EP Communication for EP Patent Application No. 17767639.2, dated Oct. 26, 2018.
EP Communication for EP Patent Application No. 17767639.2, dated Oct. 9, 2019.
Response for EP Patent Application No. 17767639.2, filed Apr. 8, 2020.
English Translation Search Report for CN Patent Application No. 2017800273068, Aug. 12, 2020.
English Translation Office Action for CN Patent Application No. 2017800273068, Aug. 12, 2020.
Official Communication dated Oct. 26, 2018; for European Patent Application No. 17767639.2.
EP Search Report dated Sep. 19, 2019; or European Patent Application No. 17767639.2.
EPO communication dated Oct. 9, 2019;or European Patent Application No. 17767639.2.
Response filed Apr. 8, 2020; or European Patent Application No. 17767639.2.
Amplatzer Cardaic Plug, uploaded Sep. 12, 2011 to YouTube.com.
ASD Occlusion System, uploaded Feb. 26, 2013 to YouTube.com.
Bergmann, Watchman and Watchman Flex step-by-step case-based discussion, Cardiologicum, May 2015.

(56) References Cited

OTHER PUBLICATIONS

Reddy, Novel LAA Closure Technologies on the Horizon, Mount Sinai School of Medicine, undated.
Kar, Deviced based LAA Closure 2014, Cedars Sinai Medical Center.
Romero, Left Atrial Appendage Closure Devices, Clinical Medicine Insights: Cardiology, 2014:8, p. 45 to 52.
IPR Search Report and Written Opinion for PCT/US17/22986 dated Sep. 18, 2018.
Search Report and Written Opinion dated Mar. 17, 2017 for PCT/US2017/022986.
For Indian Patent Application No. 201817035909 (national stage of PCT/US17/22986): First Examination Report dated Jul. 23, 2021.
For Chinese Patent Application No. 2017800273068 (national stage of PCT/US17/22986): Response to First Office Action, filed Feb. 23, 2020 Decision on Rejection, dated Jul. 21, 2021 Response to Second Office Action, Nov. 4, 2021 Decision of Reexamination, Nov. 23, 2021.
For Chinese Patent Application No. 2017800273068 (national stage of PCT/US17/22986): Third Office Action, dated Nov. 30, 2021, and Response filed Jan. 4, 2022 Notification of Grant of Patent Right and Notice of Registration, issued Feb. 28, 2022.
Office Action for U.S. Appl. No. 16/085,609 dated Jun. 19, 2020.
Response to office action filed Oct. 19, 2020; for U.S. Appl. No. 16/085,609.
Interview summary dated Oct. 21, 2020; for U.S. Appl. No. 16/085,609.
Final office action for U.S. Appl. No. 16/085,609 dated Dec. 14, 2020.
Interview summary dated Feb. 12, 2021; for U.S. Appl. No. 16/085,609.
Response to final office action filed Feb. 15, 2021; for U.S. Appl. No. 16/085,609.
Advisory action dated Feb. 24, 2021; for U.S. Appl. No. 16/085,609.
Request for Continuation Examination "RCE" filed Mar. 3, 2021; for U.S. Appl. No. 16/085,609.
Office action dated Apr. 2, 2021; for U.S. Appl. No. 16/085,609.
Interview summary dated Jul. 6, 2021; for U.S. Appl. No. 16/085,609.
Final office action dated Aug. 30, 2021; for U.S. Appl. No. 16/085,609.
Interview summary dated Sep. 17, 2021; for U.S. Appl. No. 16/085,609.
Advisory action dated Sep. 22, 2021; for U.S. Appl. No. 16/085,609.
Notice allowance dated Oct. 18, 2021; for U.S. Appl. No. 16/085,609.
Issue notice dated Feb. 2, 2022; for U.S. Appl. No. 16/085,609.
Office Action for European Patent Application No. 17767639.2, dated Sep. 29, 2023.

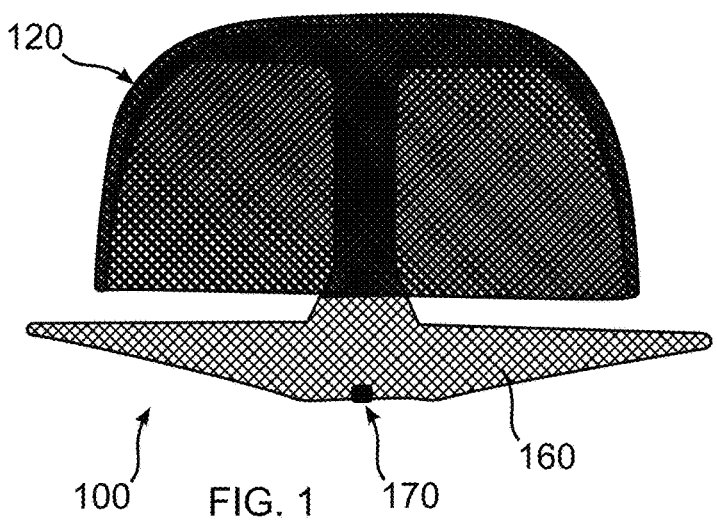
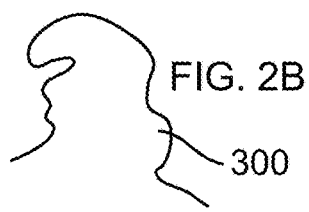
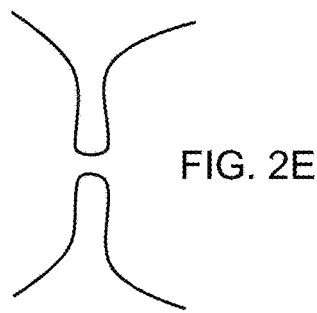
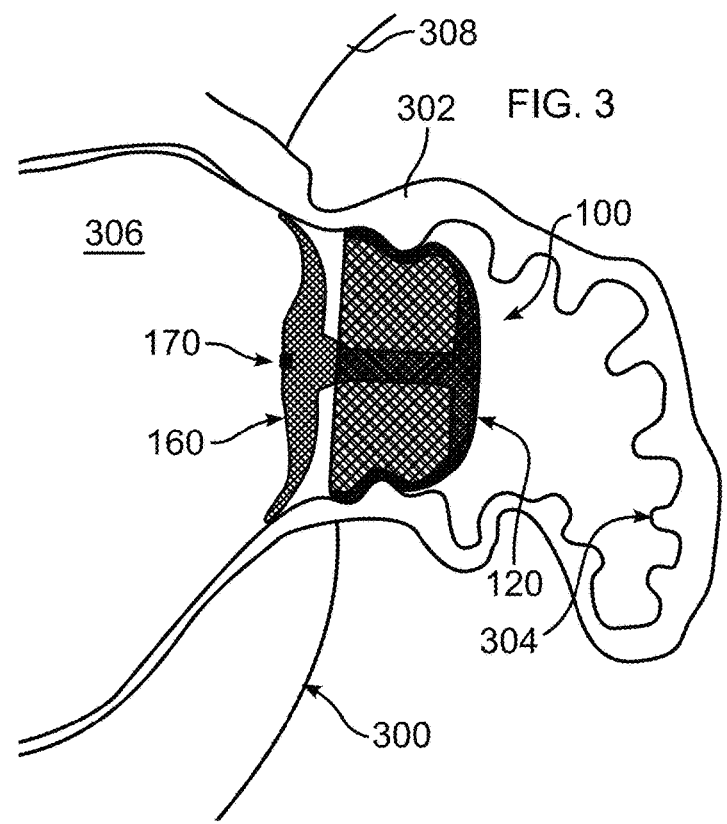

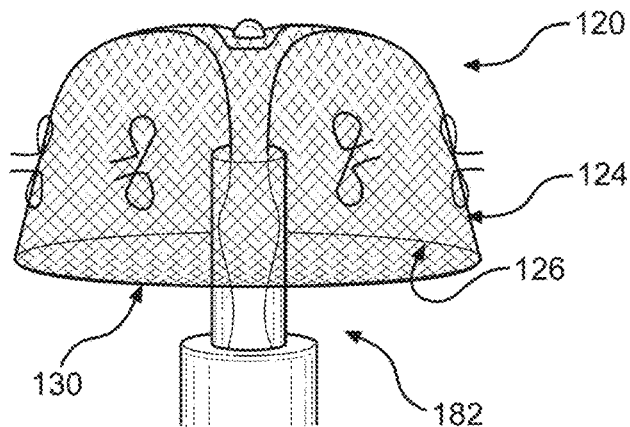
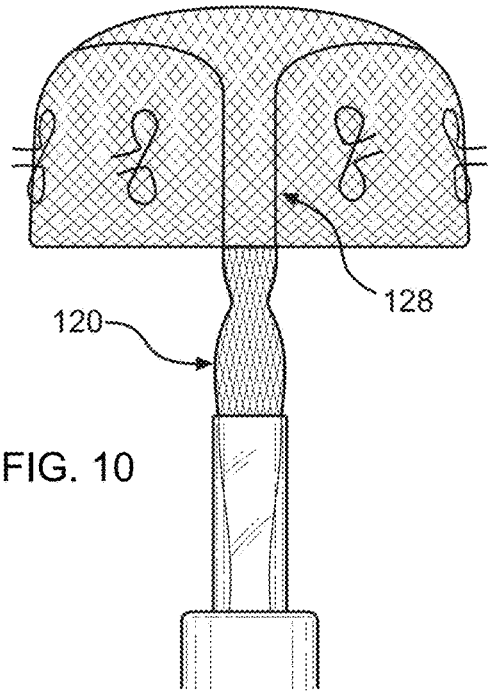
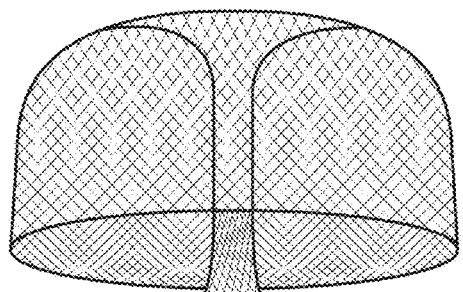
FIG. 9
FIG. 10
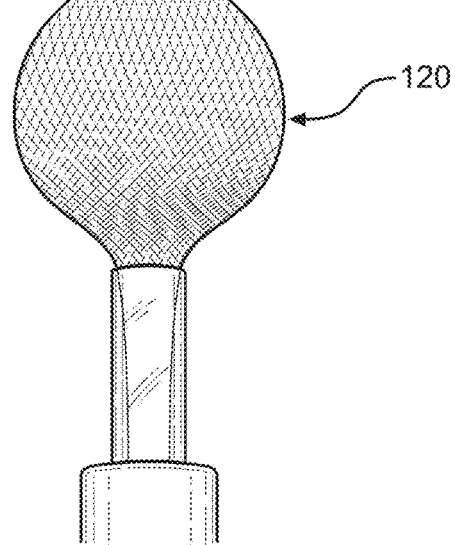
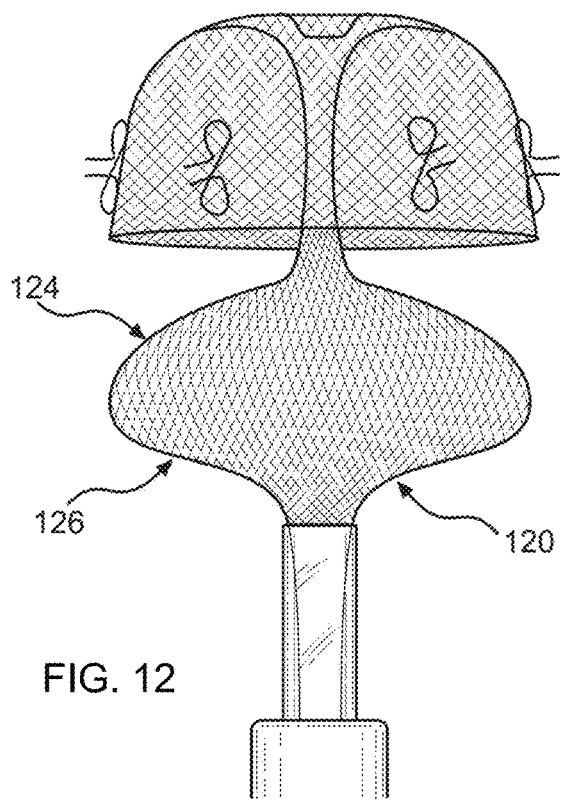
FIG. 11
FIG. 12

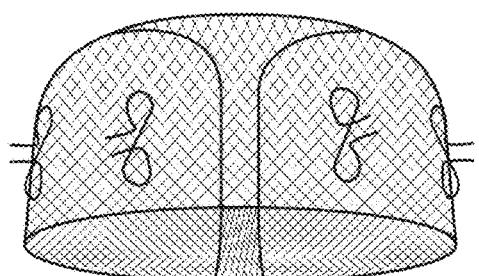
FIG. 16
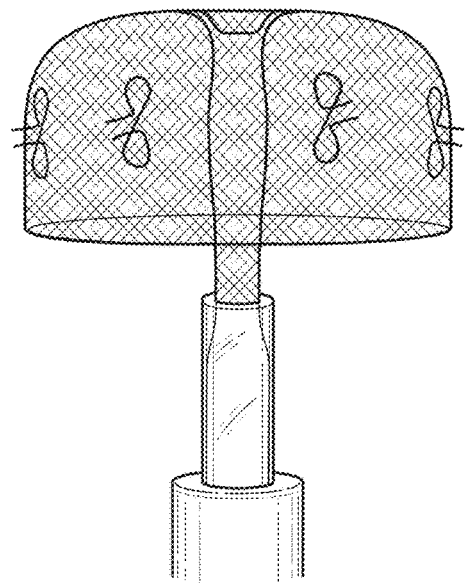
FIG. 17
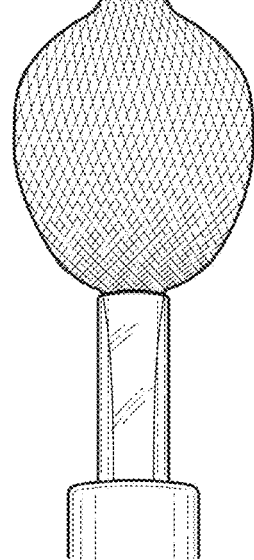
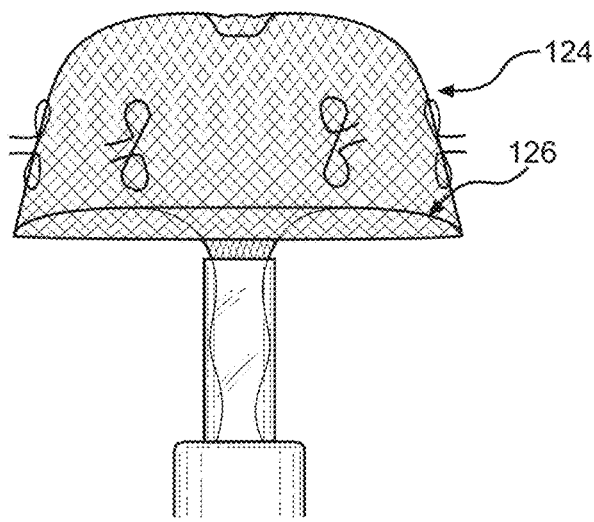
FIG. 18
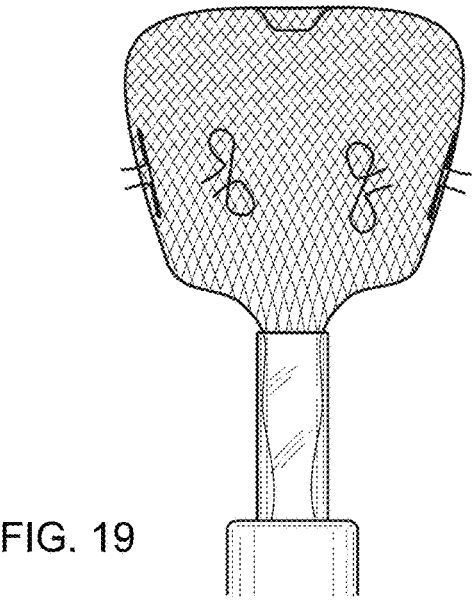
FIG. 19

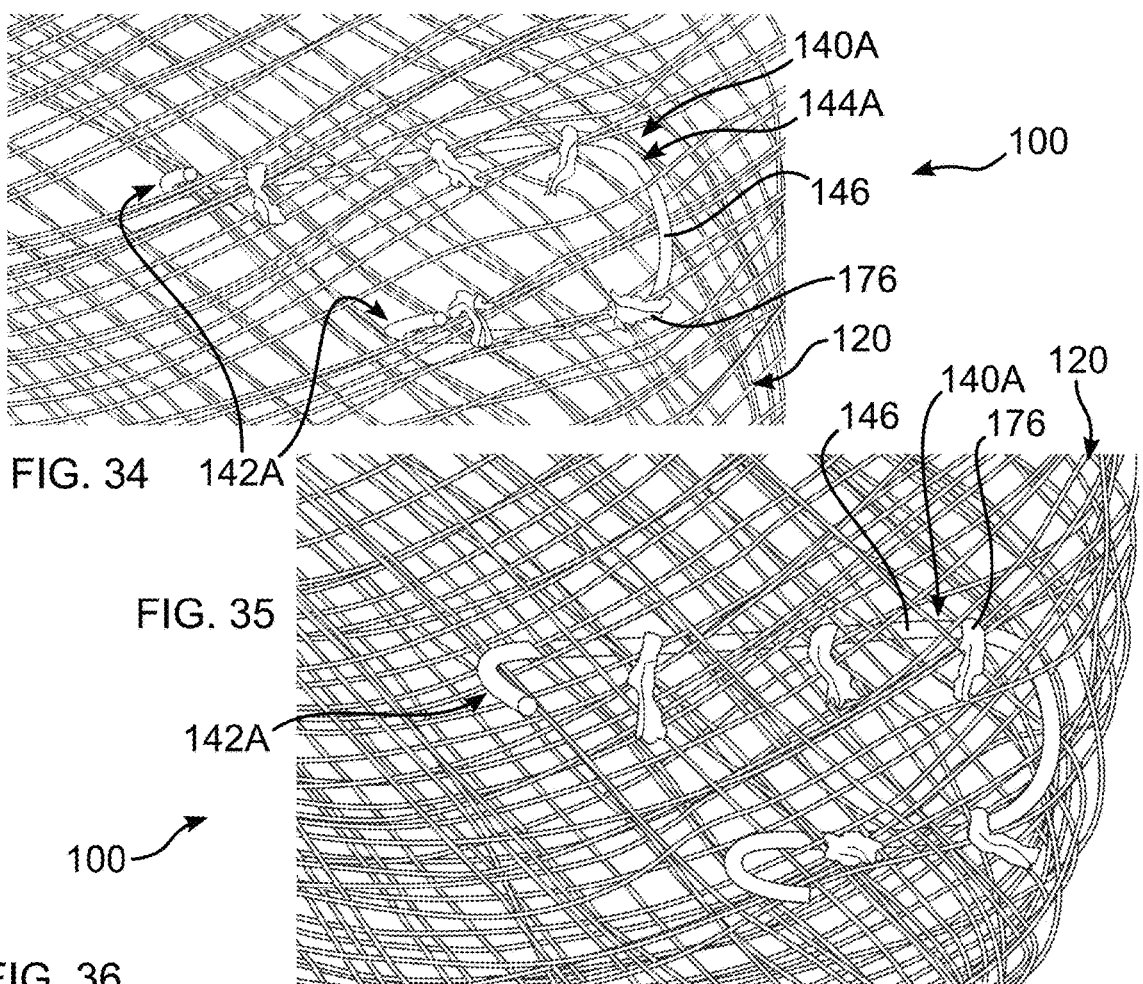
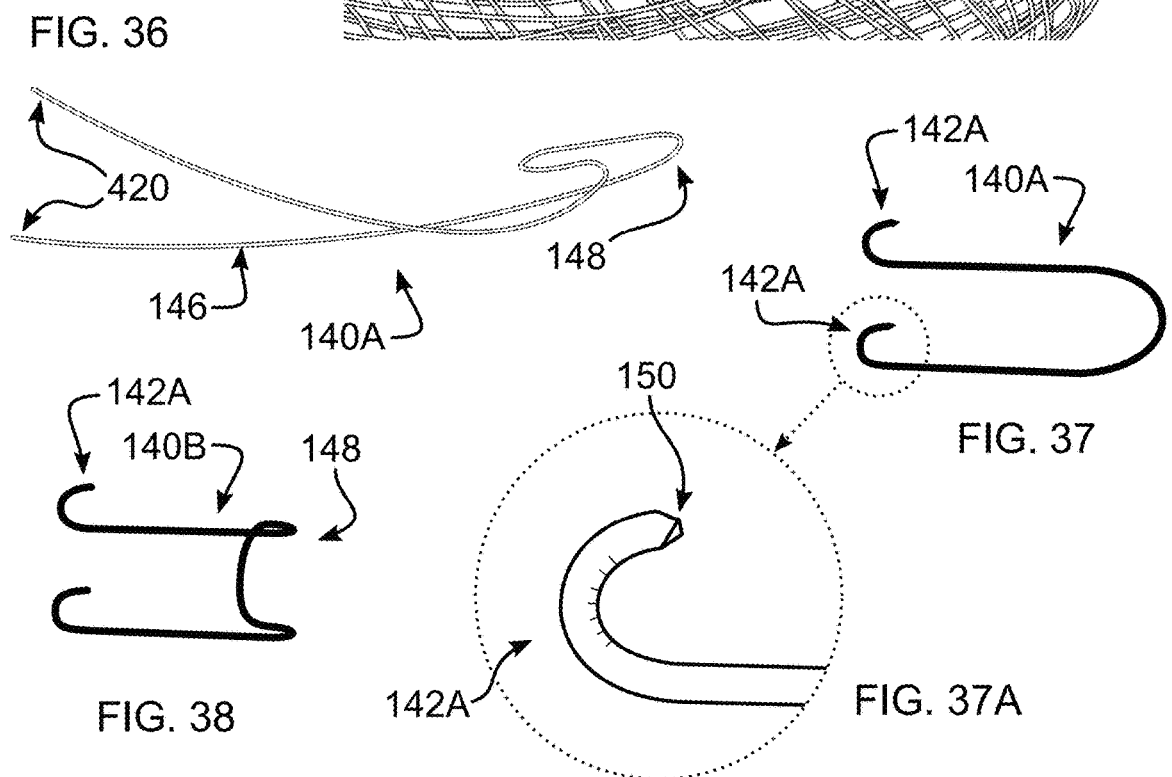

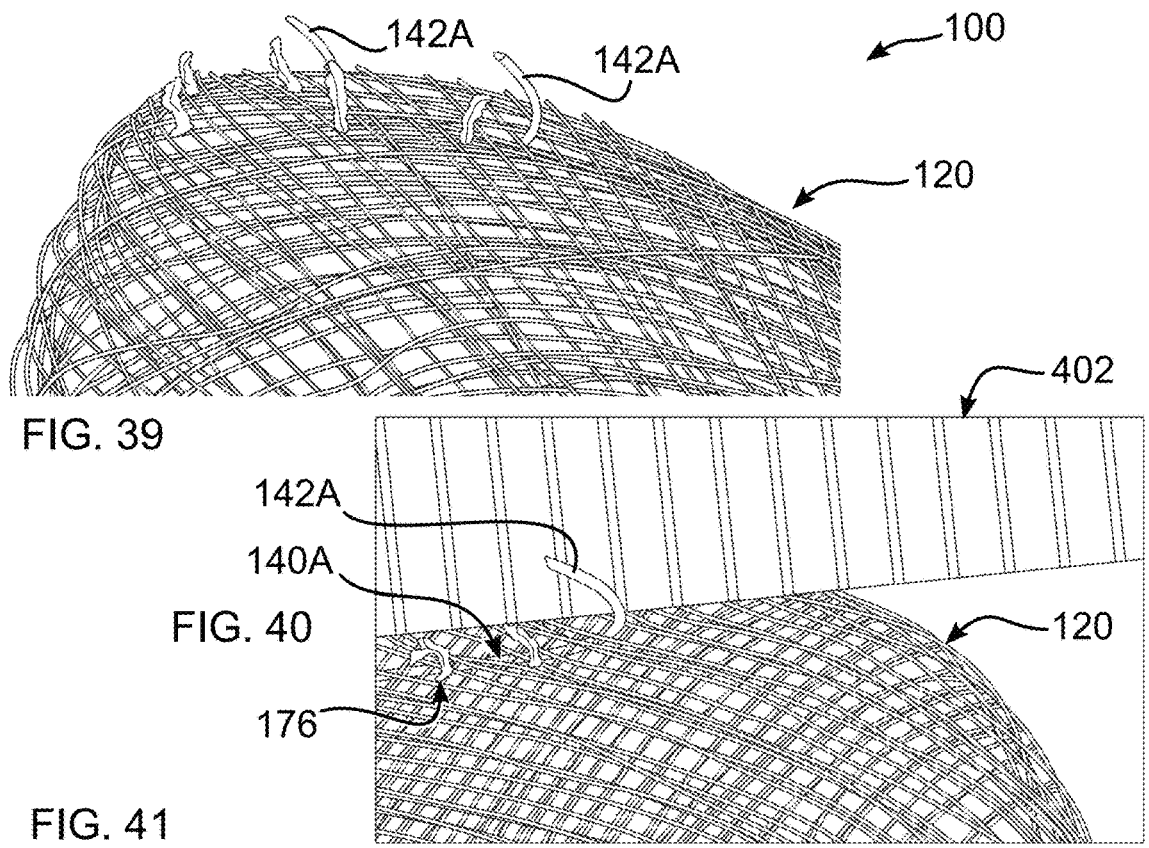
FIG. 39
FIG. 40
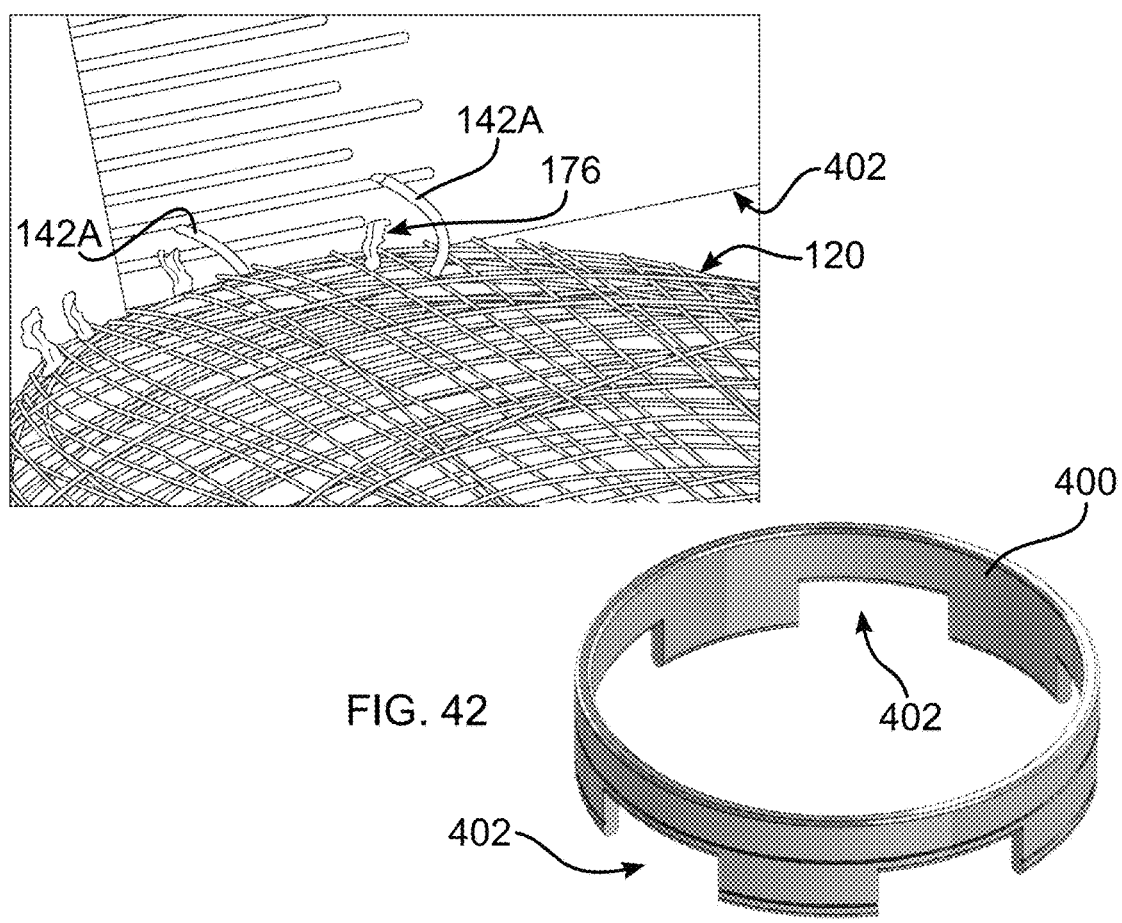
FIG. 41
FIG. 42

OCCLUDING ANATOMICAL STRUCTURES

FIELD OF THE DISCLOSURE

The disclosure relates to a system and method for occluding anatomical structures, and more particularly to a catheter delivered flexible self-anchoring cover for an internal body opening.

BACKGROUND OF THE DISCLOSURE

Occlusion devices are used to occlude or cover extra anatomical anomalies or malformations in the body which include for example appendages and aneurysms which can critically alter the normal functioning of a vessel or organ in the body. These anatomical structures can create a risk of clot formation which can lead to stroke or other serious or life threatening conditions. The risk can be greatly reduced by plugging or covering an opening into the structure.

SUMMARY OF THE DISCLOSURE

In accordance with the disclosure, a device for occluding an appendage inside a living body forming an elongate passage and having an open entrance and a hollow interior, comprises at least one elongate resilient tube formed of a mesh of shape memory alloy, the tube compressible to be delivered to the appendage within a catheter, the at least one tube self-expanding as the tube is released from the catheter to contiguously form, sequentially: an outer perimeter structure that is elongate on a side portion of the outer perimeter structure to be sized and dimensioned to flexibly conform to a longitudinal anatomy of an interior surface of the appendage extending along a longitudinal axis of the appendage when the device is deployed within the appendage; an inner perimeter structure sized and dimensioned along an elongate contact area to flexibly and conformingly contact an interior of the outer perimeter structure to thereby mutually conform to the interior surface of the appendage together with the outer perimeter structure when the device is deployed within the appendage, the inner perimeter structure forming a snap fit with the outer perimeter structure when the device is deployed within the appendage due to a shape memory effect of folding of the device, wherein the inner perimeter structure frictionally engages the outer perimeter structure along the elongate contact area to thereby resist displacement of the outer perimeter structure along the longitudinal axis of the appendage, the inner perimeter structure and the outer perimeter structure together forming a single double-walled perimeter structure defining a hollow interior; a plurality of hooks each affixed to the outer bell-shaped structure to extend away from the outer bell-shaped structure, forming a barb having J-shape, and forming a sharp free end profile at an end of the barb.

In variations thereof, the plurality of hooks define rows encircling a perimeter of the device; the hook having a height of 1.0 mm+/−0.25 mm as measured from a curved end of the J-shape to the sharp free end profile; the hook having a length of 1.5 mm+/−0.25 mm as measured from a surface of the outer perimeter structure from which the barb extends to the sharp free end profile of the barb; the hook can be pulled straight when the elongate resilient tube is returned to the catheter, and the hook will re-form the J-shape after the elongate resilient tube is again released from the catheter; at least two hooks are formed from a single wire bent to form a U-shape before the wire is affixed to the outer bell-shaped structure; a curved portion of the U-shape is folded upon itself when the single wire is affixed to the outer bell-shaped structure; and/or the at least one elongate resilient tube includes first and second elongate resilient tubes, the second elongate resilient tube disposed within the first elongate resilient tube.

In a further variation thereof, a method for occluding an appendage inside a living body, comprising delivering the device by a catheter and positioning the device in the appendage to engage the plurality of hooks with body tissue.

In variations of the method, each of the plurality of hooks are sized to pierce the body tissue without passing through an external wall of the appendage; the appendage is the left atrial appendage (LAA); and/or the at least one elongate resilient tube is a single elongate resilient tube, which is partially involuted to form inner and outer sleeves that form the double-walled bell-shaped structure, tubular connector, and plate-shaped structure.

In another variation thereof, the device further includes a tubular connector having a diameter substantially smaller than the double-walled perimeter structure and the opening of the appendage, the tubular connector extending away from an apex of the double-walled perimeter structure and through the hollow perimeter interior.

In a further embodiment of the disclosure, a device for occluding an appendage inside a living body forming an elongate passage and having an open entrance and a hollow interior comprises at least one elongate resilient tube formed of a mesh of shape memory alloy, the tube compressible to be delivered to the appendage within a catheter, the at least one tube self-expanding as the tube is released from the catheter to contiguously form, sequentially: an outer bell-shaped structure that is elongate on a side portion of the bell-shape to be sized and dimensioned to flexibly conform to a longitudinal anatomy of an interior surface of the appendage extending along a longitudinal axis of the appendage when the device is deployed within the appendage; an inner bell-shaped structure sized and dimensioned along an elongate contact area to flexibly and conformingly contact an interior of the outer bell-shaped structure to thereby mutually conform to the interior surface of the appendage together with the outer bell-shaped structure when the device is deployed within the appendage, the inner bell-shaped structure forming a snap fit with the outer bell-shaped structure when the device is deployed within the appendage due to a shape memory effect of folding of the device, wherein the inner bell-shaped structure frictionally engages the outer bell-shaped structure along the elongate contact area to thereby resist displacement of the outer bell-shaped structure along the longitudinal axis of the appendage, the inner bell-shaped structure and the outer bell-shaped structure together forming a single double-walled bell-shaped structure defining a hollow bell interior; a tubular connector having a diameter substantially smaller than the double-walled bell-shaped structure and the opening of the appendage, the tubular connector extending away from an apex of the double-walled bell-shaped structure and through the hollow bell interior; and a plurality of hooks each affixed to the outer bell-shaped structure to extend away from the outer bell-shaped structure, forming a barb having J-shape, and forming a sharp free end profile at an end of the barb.

In variations thereof, the plurality of hooks define rows encircling a perimeter of the device; the hook having a height of 1.0 mm+/−0.25 mm as measured from a curved end of the J-shape to the sharp free end profile; and/or the hook having a length of 1.5 mm+/−0.25 mm as measured from a surface of the outer perimeter structure from which the barb extends to the sharp free end profile of the barb.

In other variations thereof, the hook can be pulled straight when the elongate resilient tube is returned to the catheter, and the hook will re-form the J-shape after the elongate resilient tube is again released from the catheter; at least two hooks are formed from a single wire bent to form a U-shape before the wire is affixed to the outer bell-shaped structure; and/or a curved portion of the U-shape is folded upon itself when the single wire is affixed to the outer bell-shaped structure.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein:

FIG. 1 depicts a side view of an occlusion device of the disclosure;

FIG. 2A depicts a cactus type left atrial appendage (LAA);

FIG. 2B depicts a windsock type LAA;

FIG. 2C depicts a cauliflower type LAA;

FIG. 2D depicts a chicken wing type LAA;

FIG. 2E depicts a wall or septum within the body having an opening or perforation;

FIG. 3 depicts the device of FIG. 1 secured in place within an LAA;

FIG. 9 depicts the device of FIG. 1, continuing to emerge and completing formation of the inner bell-shape structure;

FIG. 10 depicts the device of FIG. 1, continuing to emerge and forming a connector portion, and beginning to form a cover structure;

FIGS. 11-12 depict the device of FIG. 1, continuing to emerge and continuing to form the cover structure;

FIG. 16 depicts retrieval of the device of FIG. 1, the cover returning to a balloon-like shape as it is pulled into the catheter;

FIG. 17 depicts retrieval of the device of FIG. 1, the cover fully withdrawn into the catheter;

FIG. 18 depicts retrieval of the device of FIG. 1, the inner bell-shape withdrawn;

FIG. 19-21 depicts retrieval of the device of FIG. 1, the outer bell-shape in progressive stages of being withdrawn;

FIG. 34 depicts a perimeter structure of an anchor of the disclosure including a U-shaped wire forming two hooked ends that is affixed to the perimeter structure;

FIG. 35 depicts an alternative view of the hooks of FIG. 34;

FIG. 36 depicts the U-shaped wire of FIG. 34 prior to being assembled into and affixed into the perimeter structure, the U-shaped curved end folded onto itself;

FIG. 37 depicts the U-shaped wire of FIG. 34, each end cut to a predetermined length and formed with J-shaped hooks at each free end;

FIG. 37A depicts a detail of a J-shaped hook of FIG. 37;

FIG. 38 depicts the U-shaped wire of FIG. 37, the U-shaped curved end folded onto itself;

FIG. 39 depicts a detailed view of the hooks of FIG. 34, together with sutures used to affix the U-shaped wire and formed hooks to the perimeter structure;

FIG. 40 depicts a ruler measuring a height of the hooks of FIG. 39;

FIG. 41 depicts a ruler measuring a length of the hooks of FIG. 39;

FIG. 42 depicts a measuring tool to validate a height, length, and shape of the hooks of FIG. 39;

DETAILED DESCRIPTION OF THE DISCLOSURE

Figure 4:
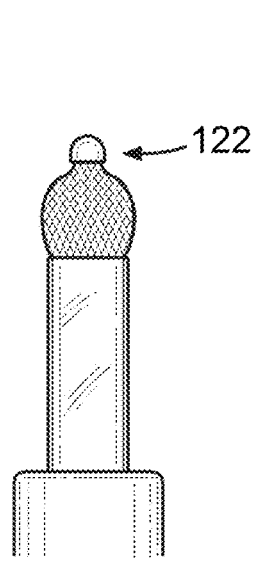
FIG. 4 depicts the device of FIG. 1 beginning to emerge from a catheter.

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language). The term "coupled," as used herein, is defined as "connected," although not necessarily directly, and not necessarily mechanically.

With reference to FIGS. 1-3, a device 100 of the disclosure includes an anchor 120 sized to conformingly engage interior sidewalls of a malformed or anomalous anatomical structure within the body (hereinafter the 'anatomical structure'), and a cover 160 sized to occlude or overlie an opening into the structure. Devices 100 of the disclosure can be used to occlude any opening of the body. Examples are shown in FIGS. 2A-2D, diagrammatically illustrating various known types of left atrial appendages (LAAs), and FIG. 2E illustrating any type of tissue wall having an undesired opening.

FIG. 3 illustrates a 'windsock' type LAA 302 of a human heart 300, in cross-section, closed off or occluded with device 100. Additionally shown in part are the left atrium 306, and the left superior pulmonary vein 308. It may be seen that an outer anchor sidewall forming a perimeter structure, or outer bell-shape 124 is conforming to a convoluted geometry of the interior surface 304 of the LAA. It may further be seen that cover 160 conforms to the surface of anatomy, in this example the interior of atrium 306, and is eventually covered over by body tissue.

Device 100 is attached to a deployment cable 180 (visible in FIG. 15), and is inserted into a catheter 182 for deployment or retrieval. In the example of the LAA, the catheter is passed through a vein in the leg, and passes into the left atrium through a transseptal puncture of the interatrial septum, or by other known method. A pigtail catheter can be used to reduce a possibility of LAA perforation, and a preloaded delivery catheter can be advanced over the pigtail into the LAA, as would be understood within the art. The preloaded delivery catheter is advanced into the tip of an access sheath, and is deployed by first pushing the device into the sheath. Then, while the sheath remains in place at the mouth of the LAA, device 100 is pushed out using cable 180 which is connected to device 100. A final position can be confirmed with Transesophageal Echocardiography (TEE), intracardiac echocardiography (ICE), fluoroscopy, or any other known method.

A catheter can likewise be used to access any other body structure into which device 100 is to be deployed or retrieved. Device 100 is constructed as a mesh of resilient expandable material. In the embodiment shown, the mesh is formed from woven strands of memory wire. Alternatively, device 100 can be formed by stamping apertures in a sheet of such material. Within the catheter, device 100 forms an elongated tubular structure that is held in a compressed form. In an embodiment, the mesh is formed from a polymeric material, and can be woven from strands; stamped from a sheet which then fused along an edge to form a tube; or is molded into the form described herein. The tube can be braided or knitted, and is molded in specific shapes disclosed herein in order to be able to be compressed, delivered inside the body, and released to resume the molded shape.

Whether stamped or formed as a wire mesh, the resilient expandable material can be a shape memory metal or alloy such as nitinol, although another material that is superelastic, resilient, has a shape memory effect to resume a pre-formed shape, and is durable and biocompatible. Specific shape memory materials that can be used include copper-aluminum-nickel, and nickel titanium alloys, although other materials having similar characteristics may be used, which are either known or are to be hereinafter developed. The material can be a combination of a shape memory metal and a polymeric material, wherein the polymeric fibers are interspaced within the strands of Nitinol, as shown in the illustrations. Additionally, cladded materials can be used, for example wherein the Nitinol is cladded on the outside with platinum, gold, another biocompatible noble metal, or any other passive materials. The disclosed device 100 shapes are made by forcing the braid or the knit into a mold corresponding to the desired final shape, and then applying a prescribed heat for a predetermined time, in accordance with the requirements of the material selected, to heat set the mold shape.

In various embodiments, the tubular structure 102 (FIG. 32A) of device 100 is open at each end, or is closed at one or both ends. In the embodiment illustrated, the woven material is closed at each end. At a distal end 132 which emerges from the catheter into the body first, the woven material is gathered into a crimp 122, although other forms of closure can be carried out, including using adhesive, brazing, soldering, fusing, sewing, or a clip or other fastener, for example. At a proximal end of device 100, material is gathered and attached to a connector 170, so that device 100 can be releasably attached to deployment cable 180. Attachment can be by any means, including a threaded connection or twist-lock connection, for example, and can be fabricated using a biocompatible metal or plastic material, for example. By gathering and crimping distal end 132, a potential for piercing of body tissue is reduced. In an embodiment, connector 170 includes a female threaded portion connected to device 100, and a mating male threaded portion at the end of cable 180. Connector 170 enables cable 180 to push device 100 out of the sheath and into the anatomical structure where device 100 can be released by unthreading connector 170. If needed, cable 180 can be rethreaded to connector 170, whereupon device 100 can be retrieved from the body by pulling cable 180.

Device 100 is pushed by deployment cable 180 through catheter 182. Accordingly, the material of device 100 must be sufficiently stiff to resist collapsing and allowing cable 180 to advance past device 100. As portions of device 100 are released from catheter 182, the memory function of the shaped memory metal causes the formation of predetermined shapes, as shown in the Figures and as described herein.

Figure 5:
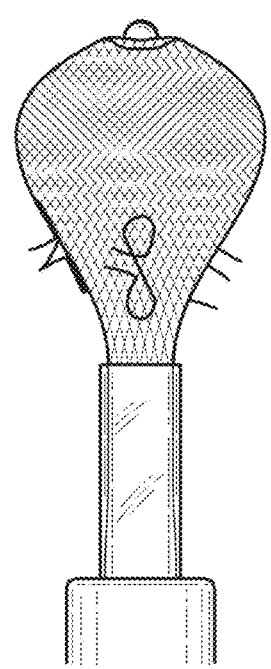
FIG. 5 depicts the device of FIG. 1, continuing to emerge and beginning to form an outer bell-shape structure.
Figure 6:
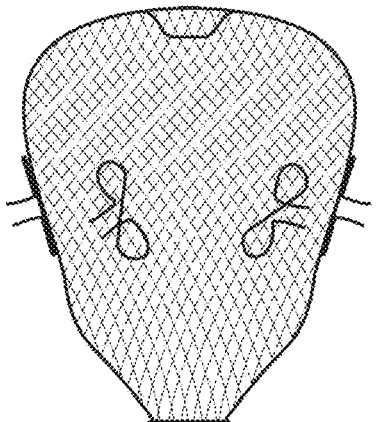
FIG. 6 depicts the device of FIG. 1, continuing to emerge and form the outer bell-shape structure.
Figure 7:
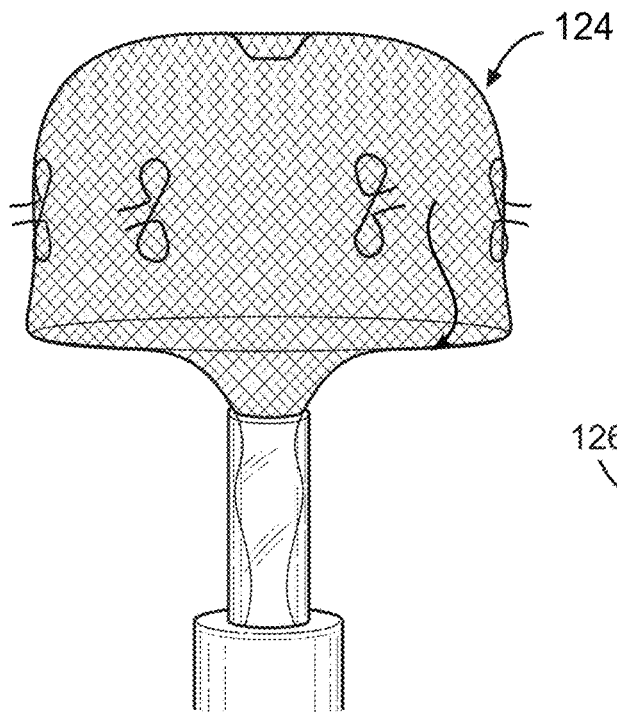
FIG. 7 depicts the device of FIG. 1, continuing to emerge and completing formation of the outer bell-shape structure.

In FIG. 4, crimp 122 at distal end 132 emerges from catheter 180 first. It may be seen that the woven structure of device 100 is compressed together to enable device 100 to fit within the catheter. In FIGS. 5 and 6, device 100 self-expands based upon the resilient spring-like nature of the shape memory alloy. Initially, this self-expansion forms a balloon-like structure, as the mesh is permitted to expand upon release from the catheter. In FIG. 7, an edge appears, and a general outline of an outer bell-shape 124 of anchor 120 becomes evident. As can be seen in FIG. 7, the bell-shaped structure is hollow, and is formed with a single wall.

Figure 8:
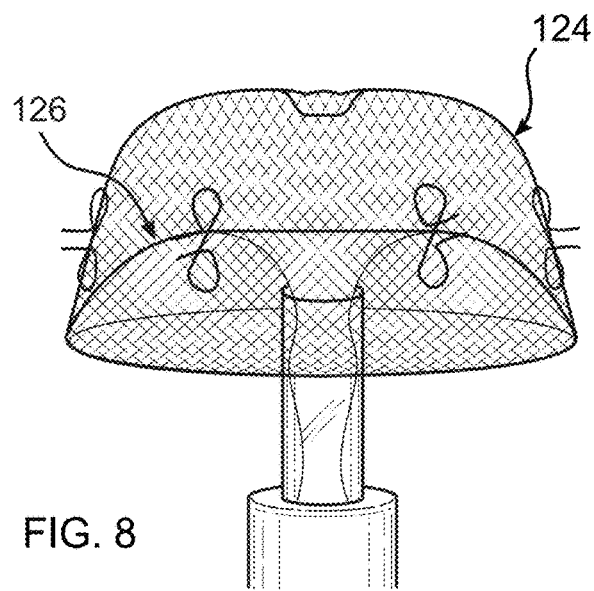
FIG. 8 depicts the device of FIG. 1, continuing to emerge and beginning to form an inner bell-shape structure.

In FIG. 8, a lower edge 130 reverses upon itself, and an inner perimeter structure, in this example forming a corresponding bell-shape 126, forms within the outer bell-shape 124. In FIG. 9, it may be seen that inner bell-shape 126 abuts, and reinforces, outer bell shape 124, forming the hollow, double-walled bell shape of anchor 120. Inner bell-shape 126 conformingly engages an inner side of outer bell-shape 124, and thereby locks outer bell-shape into conforming engagement with body tissue of the anatomical structure.

Figure 13:
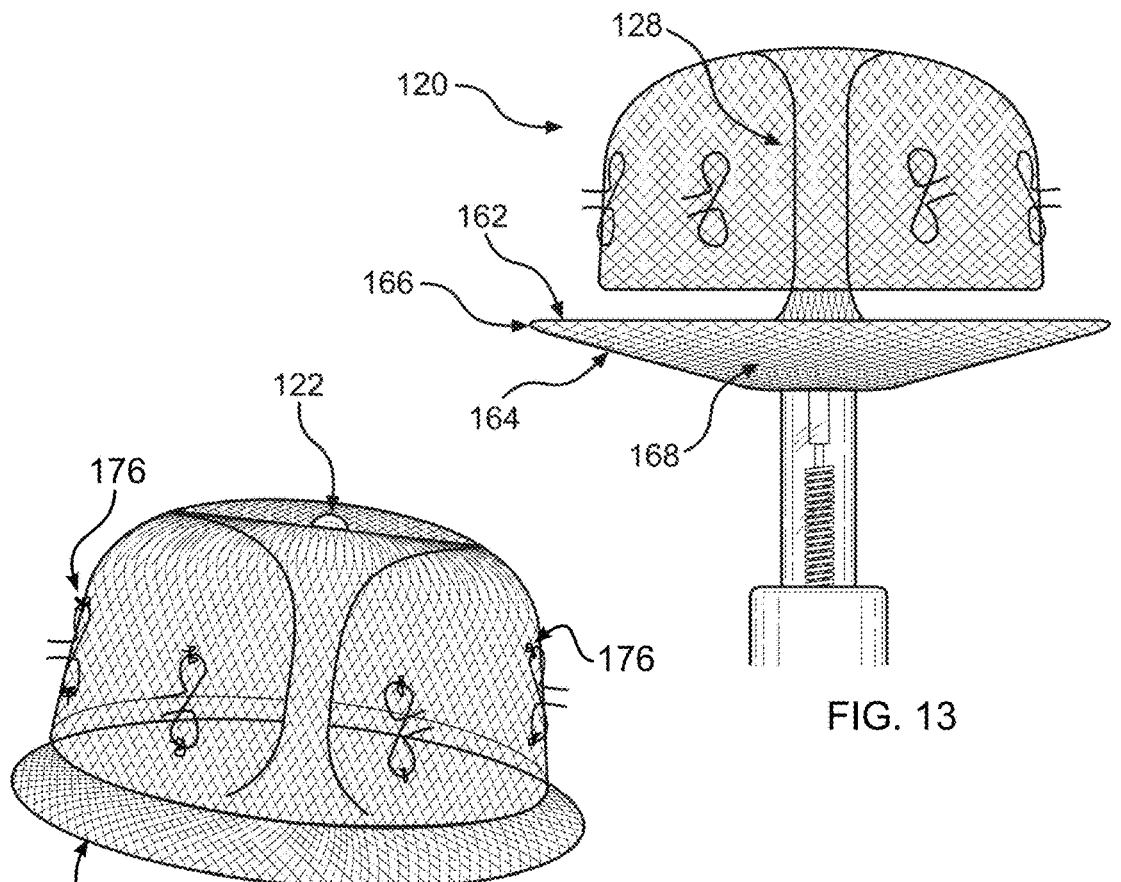
FIG. 13 depicts the device of FIG. 1, fully emerged from the catheter and fully formed.
Figure 15:
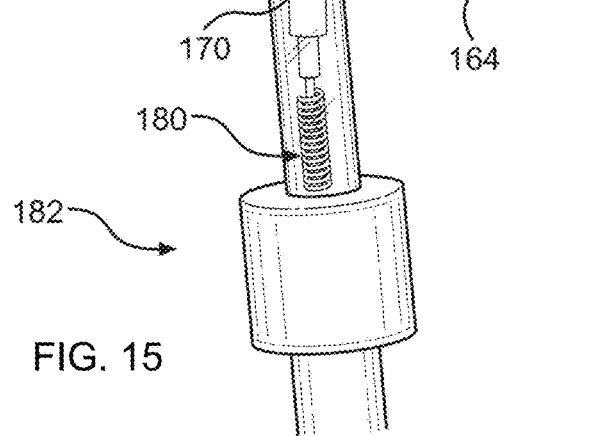
FIG. 15 depicts an attachment mechanism between the device and a deployment cable of the catheter.

In FIG. 10, the structure of cover 160 begins to emerge from catheter 182, and to expand. A tubular connector 128 extends between a distal end 132 of device 100, at an apex of inner bell-shape 126, to cover 160. In FIG. 11, it may be seen that cover 160, as with anchor 120, is formed of dual layers, which initially appear as a balloon-like structure during expansion. In FIG. 12, distal and proximal cover surfaces 162 and 164, respectively, begin to form. In FIG. 13, cover 160 has taken its final dual layer, dual plate-shape configuration. FIG. 15 is a perspective view, in which it may be seen that cover 160 has a distal surface, adjacent anchor 120, that is substantially planar, although it can be curved to conform to particular anatomy to be occluded. Other shapes can be formed which are best suited for a particular anatomical structure to be covered. Proximal cover surface 164 can lie spaced apart from distal cover surface 162, for example by forming a depression 168, so that it can resiliently press outer cover edge 166 firmly against body tissue while distal cover surface conforms to body tissue.

In an embodiment, at least proximal cover surface 164 is coated with a tissue growth factor, to promote integration of cover 160 into the body, further securing device 100 within the body, and further reducing a possibility of clot formation. It may be advantageous to coat all of device 100 with such growth factor, or to integrate the growth factor into a coating of the shape memory material of device 100, where it may be released slowly over time. Other substances can be used to coat part or all of device 100, for example including a blood thinner, antibiotic, drug, or other therapeutic substance. Device 100 may be covered with a flexible fabric, for example a polymeric fabric such as polyethylene terephthalate (PET) or other biocompatible material. This can be advantageous if it is desired to filter particles from entering or leaving the anatomical structure which are smaller than the openings in the mesh of device 100. Similarly, a nanomaterial can be used to cover device 100.

Additionally or alternatively, nanomaterials such as platinum or gold or another passive material can be used to coat the occluding device. In such coatings, each individual wire is coated using vapor deposition technology or nano-layering technology, so that individual wires or fibers in device 100 are coated with a thin or ultrathin layer of material.

Figure 25:
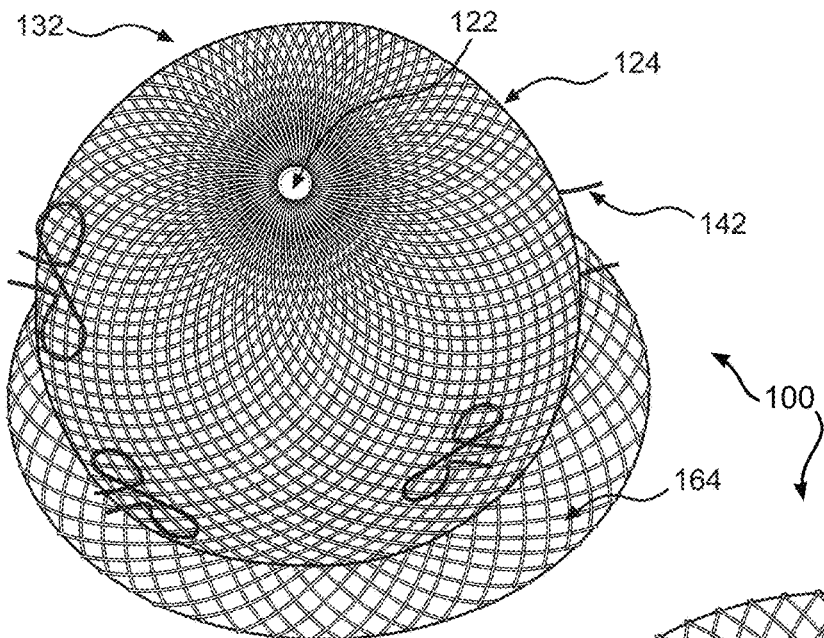
FIG. 25 depicts a top view of a device of the disclosure, the dual plate configuration including a filtering membrane.
Figure 26:
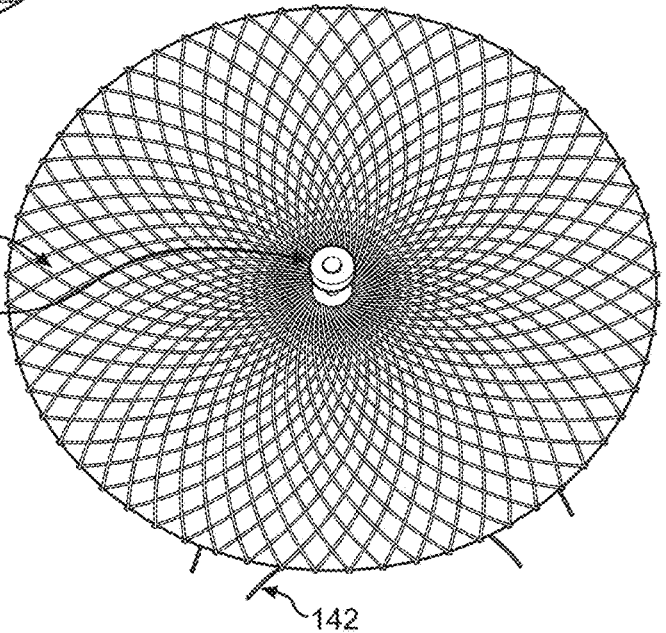
FIG. 26 depicts the device of FIG. 25, detailing a threaded connector of the disclosure.

In the embodiment of FIGS. 25-26, a polymeric filtering fabric filter 178 is inserted between proximal and distal cover surfaces 162, 164, and provides further protection from migration of clots or particles from within the anatomical structure to the blood stream. Filter 178 can be held in place by being attached to connector 170, or it can be sutured or adhered in place at least until deployment, when it is maintained in position by being constrained between surfaces 162 and 164. Filter 178 can be fabricated from any biocompatible material that is compressible during deployment, including for example PET fabric, and which has a desired mesh or pore size.

Figure 14:
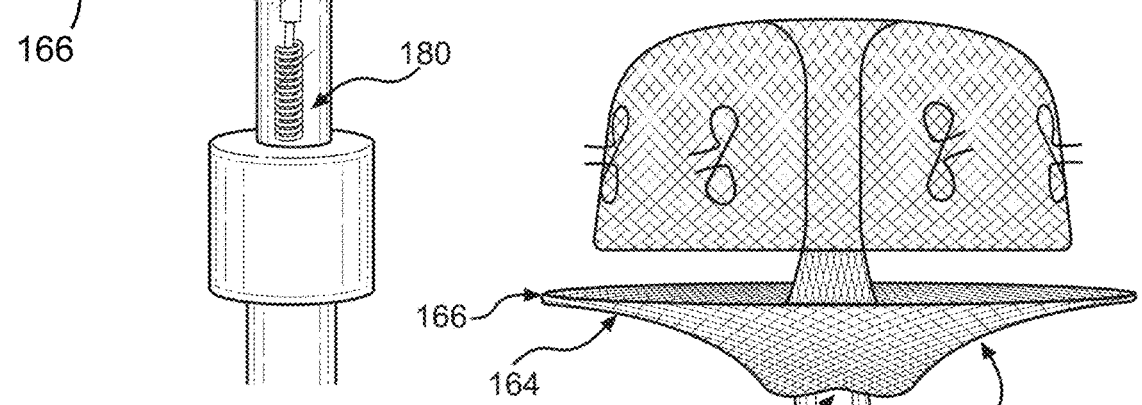
FIG. 14 depicts a perspective view of the device of FIG. 13.

In FIGS. 14-15, deployment cable 180 is visible as a rod of coiled wire, although any known construction can be used. Cable 180 can be rotated axially to unthread or otherwise disconnect cable mating connector portion 170, attached to deployment cable 180, from a device mating connector portion 170.

Figure 21:
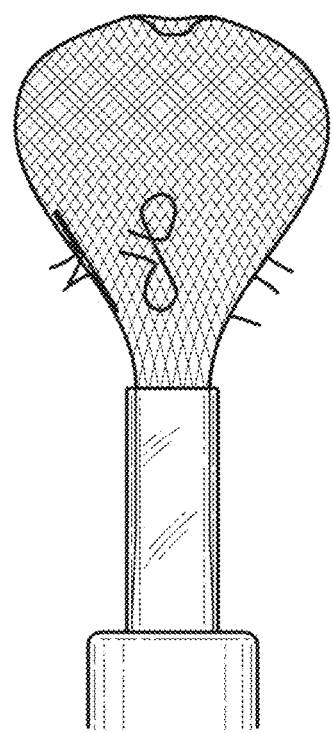
Figure 20:
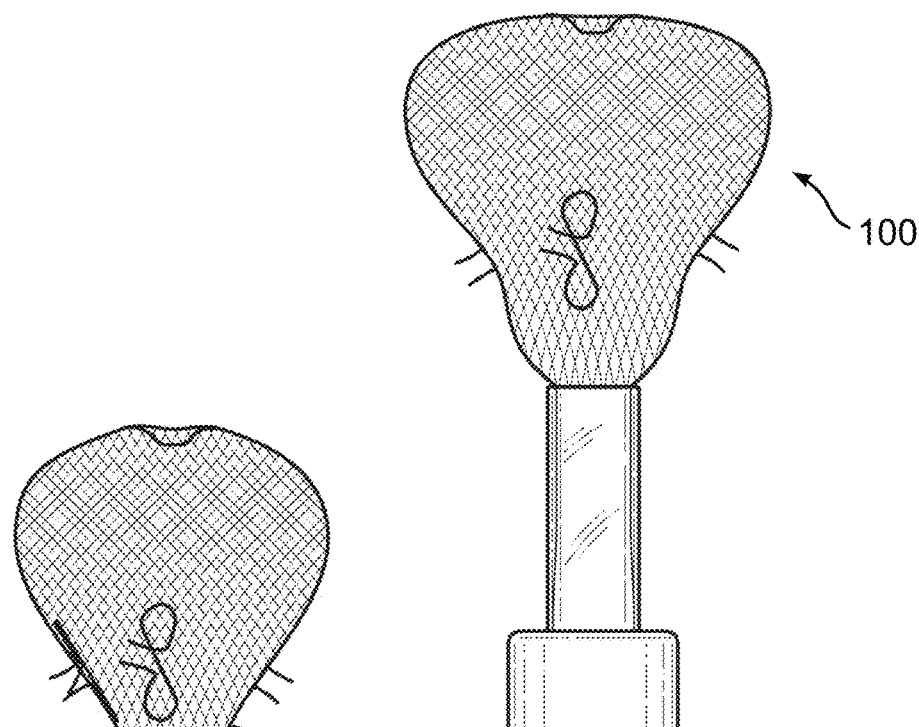
Figure 22:
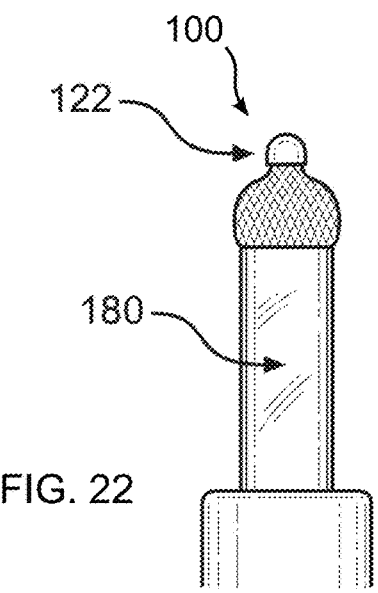
FIG. 22 depicts all but a distal end of the device of FIG. 1 withdrawn into the catheter.

In FIG. 15, device 100 begins to be recaptured or retrieved into catheter 182, causing some distortion in proximal cover surface 164. Retrieval can be carried out for repositioning device 100 within the same procedure, or for removing device 100 after an extended period of time. In FIG. 16, a collapsing pressure is applied by an end of catheter 182, and cover 160 is stretched to once again form a balloon shape, which has entered the catheter in FIG. 17. In FIG. 18, inner bell-shape 126 is pulled away from outer bell-shape 124, and is drawn into catheter 182. In FIG. 19, inner bell-shape 126 has inverted, forming a balloon shape together with outer bell-shape 124. In FIGS. 21 and 22, inner bell-shape 126 is drawn into catheter 182, and finally, in FIG. 22, outer bell-shape 124 is drawn into catheter 182, where only clip 122 is visible. Device 100 can be fully removed from the body by continuing to withdraw deployment cable 180 from catheter 182.

Figure 23:
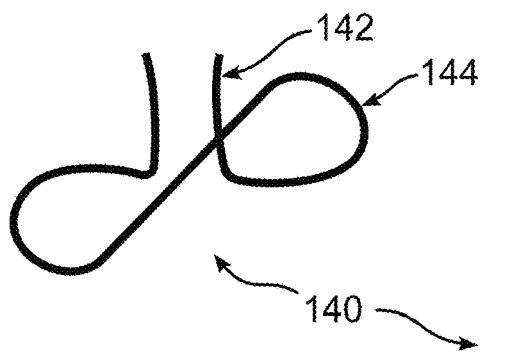
FIG. 23 depicts an isometric view of a set of hooks of the disclosure.
Figure 24:
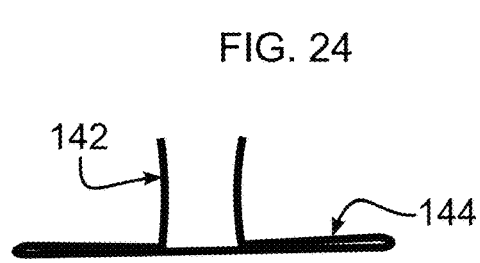
FIG. 24 depicts a side view of the hooks of FIG. 23.

Additionally visible in the Figures, and with reference to FIGS. 23-24, are hooks 140, attached to anchor 120. It should be understood that anchor 120 can securely attach to body tissue by pressing outwards against inner walls of the anatomical structure into which it has been inserted, and by resiliently conforming to the interior surface, as shown and described herein. Accordingly, hooks 140 are optional, but can be used where it is desired to provide an additional safeguard against device 100 becoming dislodged or embolized. Hooks 140 include a barb portion 142, which projects at an angle from the surface of outer bell-shape 124 of anchor 120, whereby hooks 140 can insert into body tissue as anchor 120 expands to its final conforming shape within the body.

Figure 27:
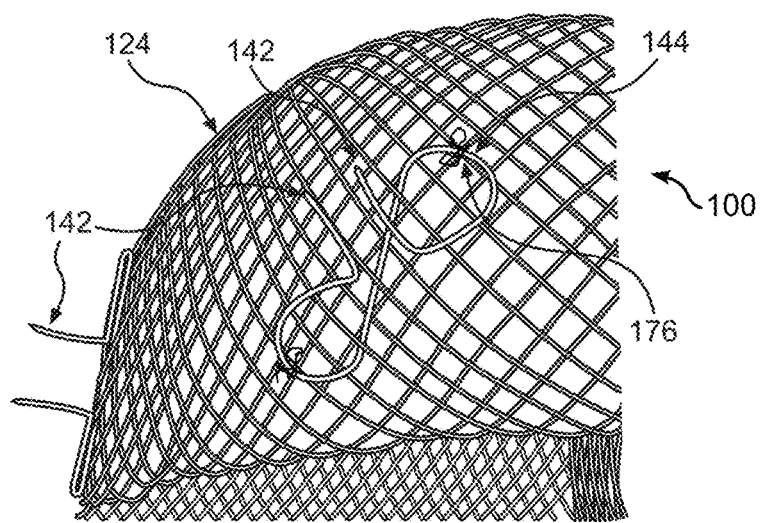
FIG. 27 is a detailed view of hooks of the disclosure, attached using sutures to an outer bell-shaped structure of a device of the disclosure.

A flattened portion 144 is woven into or otherwise attached to outer bell-shape 124, for example using sutures 176, as shown in FIGS. 14 and 27 (omitted in certain other figures, for clarity), to maintain a particular angular disposition with respect to a surface of device 100 after deployment. Where anchor 120 is formed as a stamping, barbs 142 can be bent to form the required angle. Barbs 142 are resiliently attached to flattened portion 144, so that they can be folded to lie against flattened portion 144 during deployment and retrieval of device 100 through catheter 182. The particular shape of the hook structure in FIGS. 23 and 24 is one example of how hooks can be formed and attached to a mesh material of device 100. Other shapes and styles of hooks or barbs are known in the art, and can be used with device 100 of the disclosure. Additionally, the number of hooks 140, if used at all, can be varied in accordance with the requirements of the particular deployment. The attaching sutures can be made with Polyethylene terephthalate (PET), Polypropylene, or Polytetrafluoroethylene (PTFE), for example.

Anchor 120 of the disclosure, due to its bell shape, can compress to a small proportion of its deployed diameter, enabling it to conform to, and securely attach to, a wide range of anatomical structure diameters. In particular, anchor 120 forms a bell shape with elongated sidewalls, wherein the bell is open at the bottom, facilitating close and undistorted tracking of the elongated sidewalls to the geometry of body tissue in an interior of the anatomical structure. The wide range of compression further ensures that it can maintain engagement with internal sidewalls despite substantial motion of body tissues, particularly within the heart. For occluding an LLA, for example, outer bell-shape 124 can have a diameter of as small as about 18 mm, up to about 36 mm, for typical anatomy. While each device can accommodate a wide range of variation in a diameter of the body tissue, for an optimal fit, outer bell-shape 124 can be provided in sizes at increments of 2 mm, for example 18 mm, 20 mm, 22 mm, 24 mm, 26 mm, 28 mm, 30 mm, 32 mm, 34 mm and 36 mm. Inside bell-shape 126 has a diameter of about 2 mm less than outside bell-shape 124, when device 100 is not pressed against body tissue, so would be sized at 16 mm, 18 mm, 20 mm, 22 mm, 24 mm, 26 mm, 28 mm, 30 mm, 32 mm and 34 mm.

In addition, the wide range of compression enables it to conform to substantial changes in the internal diameter of the anatomical structure over time. The wide range of resiliency, and large surface area of tissue contact, enable device 100 to be atraumatic, for embodiments without hooks 140. The extended contact area of device 100 further eliminates a need for oversizing in order to form a tight fit against body tissue, thereby avoiding tearing of body tissue, particularly in view of continuous movement of the body tissue, as in the heart. Further due to the wide range of compression, a reduced range of sizes for device 100 need to be maintained on-hand. The expanded diameter size of device 100 is determined by the range of diameters of anatomical structures to be occluded. For use in occluding LAAs, device 100 can be provided in one or more expanded diameters of between 21 and 33 mm, for example, and using, for example, a 9-Fr to 14-Fr catheter.

Cover 160, being formed of two layers of mesh, is also resilient, and can compress and deform to a substantial extent, to conform to the anatomy external to, or at the entrance to, the anatomical structure. In particular, distal cover surface 162 can contact and follow a tissue surface shape, while proximal cover surface 164, which is separated from distal cover surface 162, can maintain its shape while exerting a compressive force against distal cover surface 162.

Because device 100 is formed as a fine mesh, for example having openings of less than 1 mm, it can tightly seal against the body, and function as a filter immediately upon deployment, whether or not an overcoating fabric is provided. In addition, the mesh structure contacts body tissue with an even and diffuse application of pressure, improving grip with body tissue, while reducing trauma. The aperture sizes is determined by the pitch width and the pitch angle of the wires from which the mesh of device 100 is formed. These factors can be predetermined to form a mesh opening of a desired size, for example less than 1 mm, when the braid construction is completed. In this manner, the mesh is very compact, enabling retention of any clots inside the anatomical structure cavity.

By forming a separate anchor 120 and cover 160, device 100 enables anchor 120 to independently compress and conform to a wide variety of internal structures, while cover 160, which is separated from anchor 120 by tubular connector 128, can remain expanded to its fullest diameter, completely covering an opening to the anatomical structure. Moreover, as tubular connector 128 is highly flexible, it can bend to enable cover 160 to lie in close contact with body tissue outside of, or at an entrance to the anatomical structure, at an angle that is independent of an angular disposition of anchor 120.

Outer bell-shape 124 and inner bell-shape 126 interact to form a snap-fit or locking button, which prevents displacement of device 100 within the body. More particularly, and without being bound to a particular theory, outer bell-shape 124 conformingly engages an interior surface of the anatomical structure while it is still in a very flexible deformable balloon shape. When inner bell-shape 126 snaps into its memory shape, aligned within outer bell-shape 124, it locks the outer bell-shape 124 in this conformed configuration, by completing the shape memory inner-outer bell shape. Once the shape memory has been allowed to reform, it is resistant to further changes, particularly by displacement along a longitudinal axis extending between a proximal end at connector 170, and distal end 132, which would need to overcome the memory imposed shape. This prevents outer bell-shape 124 from rolling or otherwise moving along a surface of body tissue. Additionally, the force applied by inner bell-shape 126 against outer bell-shape 124 stiffens outer bell-shape 124 within its current conforming configuration, further resisting displacement of outer bell-shape 124 with respect to body tissue.

Figure 28:
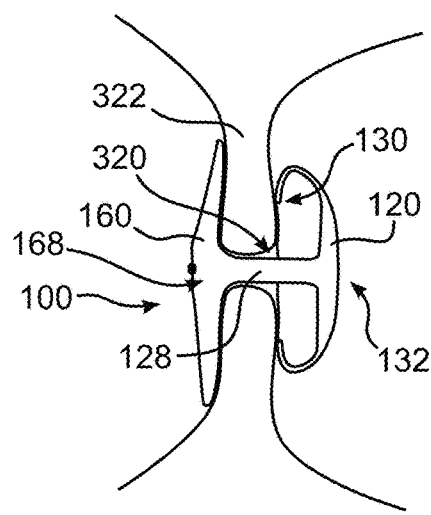
FIG. 28 depicts a cross-section of the device of FIG. 1, in place to occlude a perforation in a septum.

When occluding an opening or gap 320 in a tissue wall 322, for example of the type shown in FIG. 2E, device 100 can be positioned with cover 160 and anchor 120 on opposite sides of the wall, as shown in FIG. 28. Anchor 120 compresses by displacing lower edge 130 in a direction towards distal end 132, causing cover 160 to compress against opposite side of wall 320.

Figure 29:
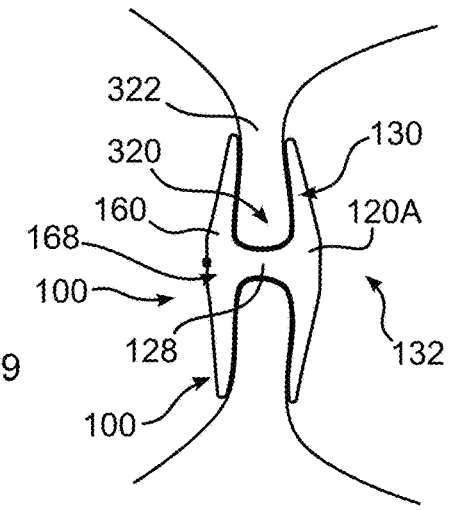
FIG. 29 depicts an alternative anchor configuration including an additional plate-shaped structure.
Figure 30:
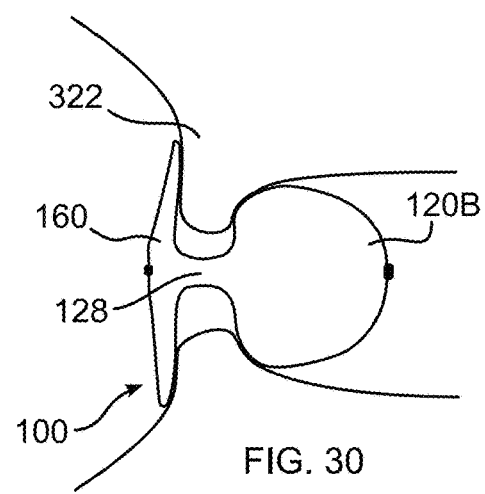
FIG. 30 depicts an alternative anchor configuration including a balloon shaped structure.
Figure 31:
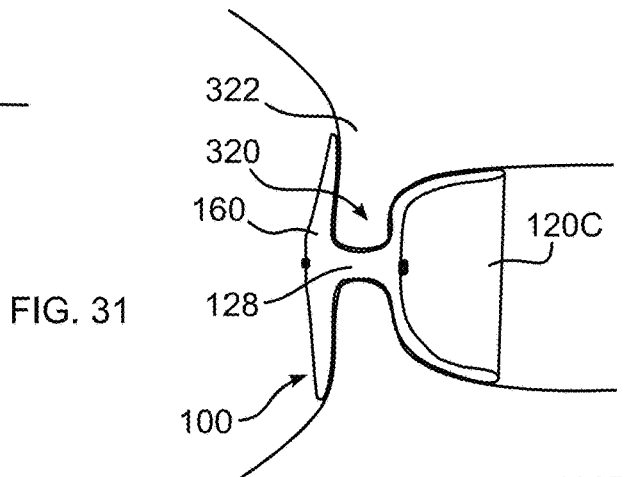
FIG. 31 depicts an alternative anchor configuration including a reverse bell-shaped structure.

While the inventors have found that anchor 120 is advantageously a bell-shaped structure connected to and cooperative with a plate-shaped which remains in place in the left atrium. However, device 100 can be configured for other areas of the body where the bell-shaped structure can have an alternate configuration which is better adapted to different anatomical geometry than the left atrium. For example, in other areas of the body, other structures can be formed, such as another plate-shaped structure 120A (FIG. 29), a balloon shape 120B (FIG. 30) which is generally spherical, ovoid, or pear shape, for example; or alternatively, a reverse bell 120C (FIG. 31) can be formed.

The inventor has further found that a dual layer structure 102A, 102B, 102C (FIG. 32B-33) of device 100 provides for improved pushability through the catheter and into the body, improving a resistance to twisting and further maintaining a desired post-expansion shape. Dual layers can provide for improved radial strength, and provide increased surface density for desired blocking or occlusion of anatomy after deployment, and as well as an improved scaffold for tissue growth.

Figure 32A:
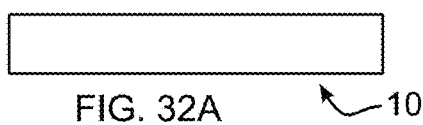
FIG. 32A diagrammatically depicts a single layer tubular structure used to form a device of the disclosure.
Figure 32B:
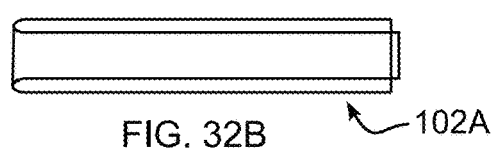
FIG. 32B depicts a dual layer structure which can be formed by turning a longer single layer tubular structure inside out, or by nesting two tubular structures.
Figure 32C:
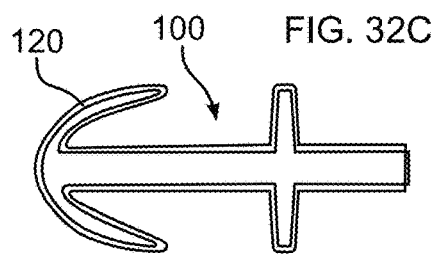
FIG. 32C diagrammatically depicts a dual layer structure forming a device of the disclosure.

FIG. 32A illustrates a single layer tubular structure 102, and FIG. 32B illustrates tubular structure 102A which has been folded in on itself to form a dual layer tubular structure 102A. This double layer structure is then formed and the desired post-expansion shape is formed as otherwise described elsewhere herein, as shown in FIG. 32C.

The diameter or thickness of the wires forming the mesh of device 100 can be selected based upon the patient size, the dimensions of the implant site and target anatomy, and the strength required. The disclosure can be carried out with any wire thickness which will yield a device 100 having the properties shown and described herein. In one embodiment not intended to be limiting, the wires are of a very thin size suitable for 144 carrier medical braider, or heavier wires suitable for a 72 carrier braider. In another embodiment, the inner layer and outer layer are formed with different braider carrier types, for example a relatively thicker 72 carrier for the inner layer, and a thinner 144 carrier for the outer layer. in this manner, the outside layer of 144 carrier braids provides relatively greater metal coverage due to the thinner wires more densely woven, while the inside layer of 72 braids provides relatively greater axial and radial strength to maintain the desired form shapes, for example cover 160 and anchor 120, and to maintain the shapes in a desired location.

Figure 33A:
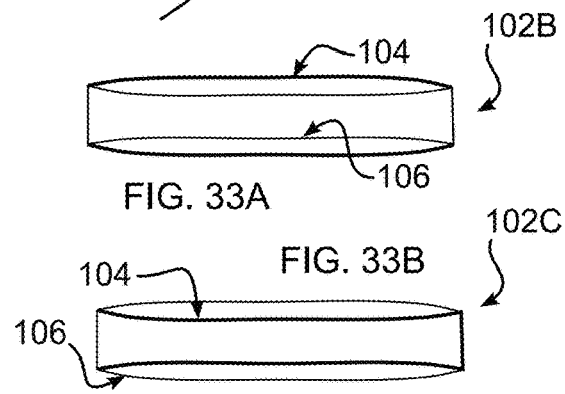
FIG. 33A depicts a dual layer structure formed of an inside tubular structure that has a different braid or mesh structure than an outer tubular structure.
Figure 33B:
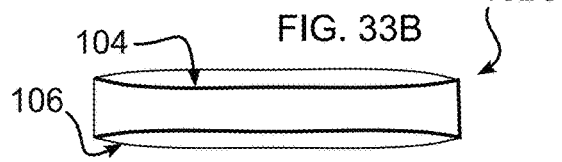
FIG. 33B depicts the inside and outside tubular structures of FIG. 33A in a mutually reversed location.

FIG. 33A illustrates, diagrammatically, an outer layer 104 which has a lower braid count, and an inner layer 106 with a higher braid count, the two layers joined at their ends. The resulting dual layer structure is then formed into the desired shape as described herein (e.g. as shown in FIG. 32C). FIG. 33B depicts the layers reversed, with the lower braid count 106 on the outside. The dual layer configurations described herein are otherwise formed and used as described herein.

Dissimilar braid sizes for the inside and outside surfaces can be joined at seams using any known method, including for example welding, brazing, soldering, weaving stamping pinching, crimping, braiding, or other method. When both layers are made from the same braid size, the inner layer can be formed by partially involuting or folding a portion of the braided material inside the other, or turning inside-out, a part of a braided tube, for example half of a tube. The interaction of the dual layers of braided or woven metals facilitates the various properties described herein, including enabling the expanded formation of structures having a desired variable depth and width to accommodate a wide variety of anatomical structures which need to be closed. Examples of such anatomical structures are found in a variety of anatomical indications like Neurological procedures, Cardiovascular procedures, Peripheral procedures, and procedures involving other systems.

With reference to FIGS. 34-35, device 100 includes hooks 140A which are affixed to anchor 120 via flexible filaments or sutures 176 as described elsewhere herein. As can be seen in FIGS. 34-35, two hook barbs 142A are formed from the ends of a single strand of drawn, stamped or otherwise formed longitudinal filament or wire 146 which is bent. In the example illustrated in FIGS. 34-38, barbs 142A form at least approximately a J shape, and wire 146 generally forms a U-shape. As depicted, wire 146 can be woven into the weave of anchor 120, after which it is further secured by sutures 176.

In accordance with the disclosure, providing a separate hook 140/140A-B enables different hook sizes and/or shapes to be used with a given anchor 120 and anchor 120 size. Further, hooks 140/140A-B can be fabricated from a different material than that of anchor 120, and can therefore have any desired attributes relative to the material of anchor 120, such as flexibility, shape memory, resilience, strength, sharpness, and other characteristics described herein. In one example embodiment, hooks 140/140A-B are formed from platinum coated nitinol having a thickness of 0.0085 inches, although thinner or thicker wire of the same or differing material can be used which provides sufficient strength and resiliency for the applications described herein.

As can be seen in FIG. 35, wire 146 of hook 140B forms a generally U-shape as in FIG. 34, and barbs 142A are not yet formed. However, it may be seen that at fold 148, a base of the U-shape is folded over upon itself. Fold 148 can be formed before or after wire 146 is woven into anchor 120, and can be attached via sutures 176 at various locations, to further secure wire 146 to anchor 120. Fold 148 provides additional points at which wire 146 can be secured by sutures 176, and additional provides resistance to twisting of wire 146, so that barbs 142A remaining extending away from a surface of anchor 120 at a desired angle, as described further elsewhere herein. Barbs 142A can be cut and formed after wire 146 has been woven into and secured to anchor 120, as described in further detail with respect to FIG. 41, below. Final shapes of hooks 140A, 140B, shown without anchor 120, are depicted in FIGS. 37 and 38, respectively.

With reference to FIGS. 39-41, it may be seen that barbs 142A emerge from the woven mesh of anchor 120 to complete the 'J' shape shown in FIGS. 34-38. In FIG. 40, a ruler is placed horizontally to lie against a surface of anchor 120 to measure a height of barb 142A which extends from the bottom of the curved portion of barb 142A to a free end of barb 142A, and in FIG. 41, the ruler is placed to extend vertically away from the surface of anchor 120 to measure a length of the barb 142A which extends from a surface of anchor 120 to the free end of barb 142A.

Accurate measurement of the barbs 142/142A in the design and production of devices 100 of the disclosure enables exploiting the close conforming nature of the double layer conforming contact of anchor 120 with the LAA interior that is provided by the disclosure. More particularly, it is desired to penetrate completely into the wall of the LAA with barb 142/142A, without passing completely through the LAA wall, and more particularly, without endangering penetration of, or actually penetrating the left superior pulmonary vein 308, which passes closely by or in contact with the LAA. The close conforming nature of devices 100 of the disclosure provides additional control of an extent of penetration of barbs 142/142A, by limiting movement of the barb with body tissue, which would otherwise be affected by the continuous motion of the heart, which would repeatedly urge any contacting device into varying levels of contact with body tissue.

The disclosure thus addresses a limitation of the prior art, wherein if a gap exists between a device and body tissue of the LAA at a location of a barb, the barb would be urged into body tissue to varying extents by the beating heart, hindering anchoring, and endangering over-penetration. Moreover, the prior must choose a barb size that is long enough to cross any such gap, rending the barb too long if the device is moved closer to body tissue during beating of the heart.

As barbs 142/142A are held fully inserted into body tissue, a length, height, and shape can be chosen which optimizes penetration and contact of the barb with body tissue of the LAA, while minimizing a chance of penetration. Further, in accordance with the disclosure, during deployment, cover 160 interacts with bell-shaped portions 124/126 to draw cover 160 and the bell-shaped structure 124/126 towards each other, fully seating barbs 142/142A, while an extent of penetration is limited by the close conforming contact of inner and outer bell-shaped portions and the LAA, as described in detail elsewhere herein.

The inventors have found that an optimal penetration depth in adults, reflected in the length and height of barb 142/142A detailed herein, provides sufficient contact with the LAA for secure anchoring, while minimizing risk of penetration. For substantially smaller or larger anatomy, these values can change accordingly. The J-shape of barbs 142A is selected to penetrate vertically to an optimal extent, while enabling further penetration horizontally, obtaining the benefit of greater contact with body tissue, without substantial risk of penetrating too deeply, or piercing the LAA.

The inventors have found that for typical adults, the height and length detailed herein are optimal for anchoring barb 142 within tissue of the LAA, without causing complete penetration of the LAA, while able to bridge gaps between the outer bell-shape of anchor 120 and body tissue of the LAA, for the various LAA tissue shapes, such as chicken wing, mushroom, and other shapes, some of which are shown as examples in FIGS. 2A-2D.

Horizontal penetration length, and thus an overall height of barb 142A is selected to ensure that even if barb 142A does not completely maintain a J shape during penetration, the overall depth of penetration will not be excessive. The inventors have found an overall height for typical adults of 1.0 mm+/−0.25 mm to be optimal for a barb 142A having a length of 1.5 mm+/l 0.25 mm. These values can additionally vary based upon the flexibility of barb 142A.

Flexibility of barb 142/142A (collectively barb 142) is further determined by using a material which has a shape memory, such as nitinol and the like. In an embodiment, hook 140/140A-B (collectively hook 140) are formed from Nitinol coated with platinum, which is secured to anchor 120 by sutures, as shown in the drawings, or by welding, brazing, soldering, or any other means which is biocompatible and of sufficient strength, and which will bind hook 140 until device 100 is secured by tissue ingrowth/overgrowth. Flexibility is additionally determined by a cross-sectional width and shape of hook 140 material. In an embodiment, hook 140 material has a round cross-section of round wire having a diameter of 0.085 inches. Shape memory is additionally enhanced by heat setting the shape memory material, whereby the barbs can be straightened and drawn back into the implantation catheter and then redeployed if desired, whereby barbs 142 will resume the original deployment shape.

A choice of material and cross-sectional shape and diameter are selected to enable device 100 to be withdrawn into the sheath after barbs 142 are set, where the force to at least partially straighten barb 142 to enable withdrawal is less than a force required to substantially tear body tissue into which barb 142 is set, but sufficiently rigid to prevent disengagement due to any anticipated extent of heart tissue movement.

Figure 43:
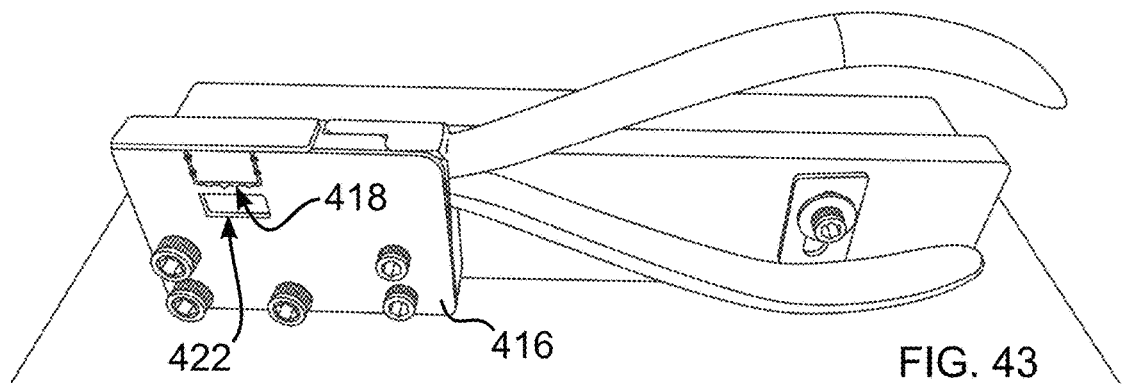
FIG. 43 depicts a back side of a tool assembly for cutting the U-shaped wire of FIG. 36 to a predetermined length, once the U-shaped wire is affixed to the perimeter structure.
Figure 44:
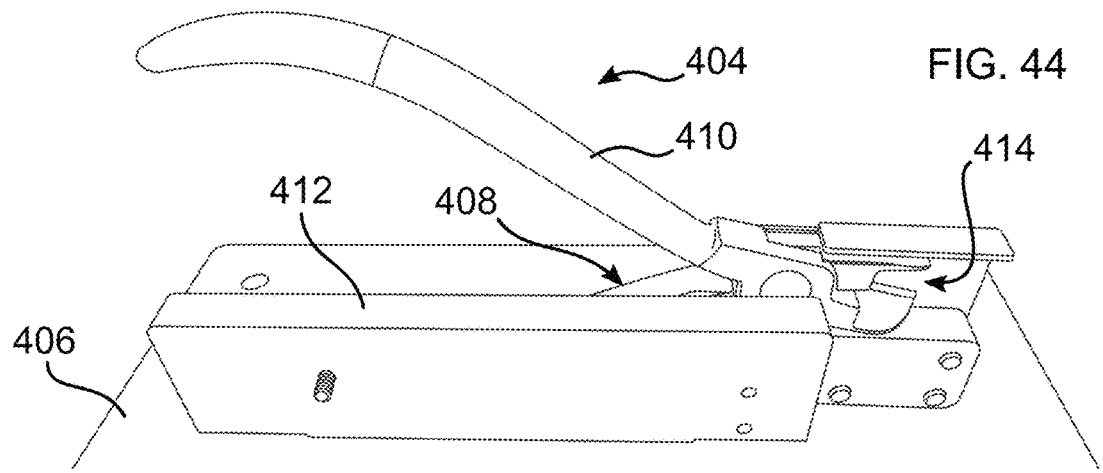
FIG. 44 depicts a front side of the tool assembly of FIG. 43.
Figure 45:
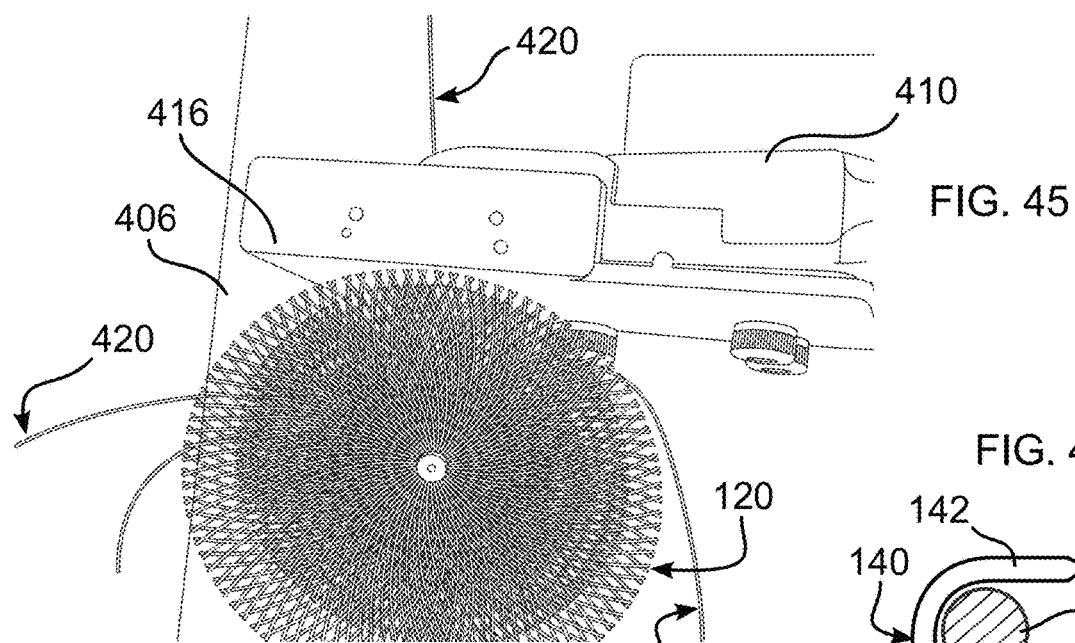
FIG. 45 depicts the U-shaped wires of FIG. 36 assembled onto and affixed to the perimeter structure of an anchor of the disclosure, a free end of a U-shaped wire inserted between cutting blades of the tool assembly of FIG. 43, in preparation for cutting the free end to a predetermined length with respect to a surface of the perimeter structure.

Referring now to FIGS. 43-45, a tool 404 for cutting wire, such as side-cutting snips as shown, or an end cutting nipper (not shown), is mounted to a base 406 so that a lower handle 408 is affixed to base 406, and an upper handle 410 is free to move. A vertical support 412 can be provided to facilitate attachment of lower handle 408 to base 406. Cutting jaws 414 include angled blades, such that a cut edge of hooks 140 and barb 142 end form a sharpened cut edge 150, as shown in FIG. 37A. Sharp end 150 is thus shaped with a sharpened linear edge that ensures a small defined penetration into tissue of the LAA without causing tearing. The cut edge additionally promotes a secure anchor while the heart is beating, until tissue growth prevents further movement of device 100. Likewise, sharp end 150 ensures ready penetration where the LAA has developed thickened or dense tissue.

A stop plate 416 forms a vertical wall 418 and one or more wire entry portals 418 through which each free end 420 (FIGS. 36 and 45) of hook 140A can be passed. As shown in FIG. 45, hooks 140 are first affixed to anchor 120, and then cut to length with respect to the surface from which the hook 140 emerges. This is carried out by passing one or both of free ends 420 of an affixed hook 140 each through a portal 418 to emerge on an opposite side of the stop plate to lie between the cutting jaws 414 of tool 404. The body of the anchor 120, for example outer bell-shape 124, is pressed against stop plate 416 to normalize each cut to a cut length corresponding to the height and width as measured in FIGS. 40-41, after bending to form the final shape (FIG. 46); however, stop plate eliminates the need to position a ruler and measure each cut. Stop plate 416 can be provided with portals 418 of different diameter corresponding to varying hook 140 diameters that may be used to manufacturer various devices 100.

Portals 418 can be formed by drilling through stop plate, or by first removing a portion of stop plate 416, filing or otherwise forming one or more grooves, then reattaching the removed plate to form precise portal 418 diameters as needed, as can be seen in FIG. 43. Stop plate 416 can be attached to base 406 and/or to vertical support 412, to ensure a predetermined gap exists between an anchor contacting face of stop plate 416, and a mating cutting edge of cutter jaws 414, to achieve the desired hook 140 length. If it is desired to have hooks 140 of differing lengths for a given device 100, a different tool 404 can be provided with a different gap to cutter jaws 414, or an additional plate (not shown) with a predetermined thickness can be placed between stop plate 416 and anchor 120. A view port 422 can be provided to visibly confirm that the cutter jaws 414 are open for receiving ends 420 therebetween.

Base plate, stop plate, and vertical support can be mutually attached by threaded fastener (as shown) or by adhesive, soldering, welding, clamps or other fastener, or any other suitably strong means which prevents movement of the components over time which may interfere with accurate measurement between stop plate 416 and cutter jaws 414.

Figure 46:
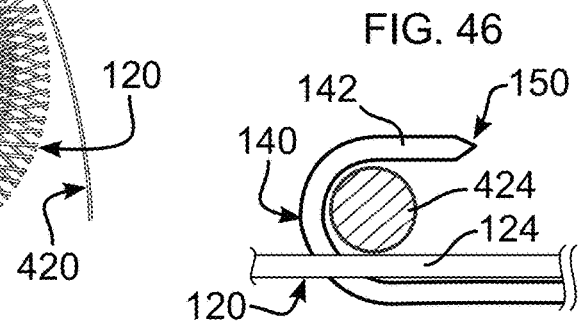
FIG. 46 depicts a mandrel positioned to facilitate and control formation of the J-shape of FIG. 34.

In FIG. 46, a mandrel 424 (shown in cross-section) is positioned against an outer surface of anchor 120 from which hook 140 emerges, and hook 140 is further bent to form the J-shape described herein. Mandrel 424 has a diameter selected to produce a hook 140 having a resulting J-shaped barb 142 having the dimensions described herein.

For volume production, a measuring and quality control tool can be used for evaluating a height, length, and shape of barbs 142A, such as dimension checking tool 400 shown in FIG. 42. More particularly, a series of cutout portions 402 are each provided with a predetermined width and height. A cutout portion 402 having a target height and length for a given product version is selected, and is positioned on top of the emerged and bent barb 142A, with the tool resting upon, and the open end of cutout portion 402 facing, the surface of anchor 120. For an ideal fit, barb 142A contacts or nearly contacts all three sides of the cutout portion, thereby enabling a quick simultaneous measurement of height, length, and shape. To further speed measurement, all remaining or unused cutout portions 402 having unneeded dimensions can be masked off, for example by tape or a cover.

All references cited herein are expressly incorporated by reference in their entirety. It will be appreciated by persons skilled in the art that the present disclosure is not limited to what has been particularly shown and described herein above. In addition, unless mention was made above to the contrary, it should be noted that all of the accompanying drawings are not to scale. There are many different features to the present disclosure and it is contemplated that these features may be used together or separately. Thus, the disclosure should not be limited to any particular combination of features or to a particular application of the disclosure. Further, it should be understood that variations and modifications within the spirit and scope of the disclosure might occur to those skilled in the art to which the disclosure pertains. Accordingly, all expedient modifications readily attainable by one versed in the art from the disclosure set forth herein that are within the scope and spirit of the present disclosure are to be included as further embodiments of the present disclosure.

Drawing References:

100 device
102/102A tubular structure
104 shape outer layer
106 shape inner layer -continued Drawing References:

120 anchor
122 crimp
124 outer bell-shape
126 inner bell-shape
128 tubular connector
130 lower edge
132 distal end
140/140A-B hooks
142/142A hook barb
144/144A hook flattened portion
146 wire
148 folded over U-shape
150 barb cut end
160 cover
162 distal cover surface
164 proximal cover surface
166 outer cover edge
170 connector
176 suture/hook attachment
178 filter
180 cable
180 deployment cable
182 catheter
300 human heart
306 left atrium
308 left superior pulmonary vein
340 LAA interior surface
400 dimension checking tool
402 ruler
404 cutter
406 base
408 lower handle
410 upper handle
412 vertical support
414 cutter jaws
416 stop plate
418 stop plate portal
420 hook free end
422 tool view port
424 mandrel

What is claimed is:

1. A device for occluding an appendage inside a living body forming an elongate passage and having an open entrance and a hollow interior, comprising:
at least one elongate resilient tube formed of a mesh of shape memory alloy, the at least one tube compressible to be delivered to the appendage within a catheter, the at least one tube self-expanding as the at least one tube is released from the catheter to contiguously form, sequentially:
an outer perimeter structure
that is elongate on a side portion of the outer perimeter structure to be sized and dimensioned to flexibly conform to a longitudinal anatomy of an interior surface of the appendage extending along a longitudinal axis of the appendage when the device is deployed within the appendage;
an inner perimeter structure
sized and dimensioned along an elongate contact area to flexibly and conformingly contact and abut an interior of the outer perimeter structure along the longitudinal anatomy to thereby mutually conform to interior surface of the appendage together with the outer perimeter structure when the device is deployed within the appendage,
the inner perimeter structure thereby frictionally engaging the outer perimeter structure along the elongate contact area to thereby resist displacement of the outer perimeter structure along the longitudinal axis of the appendage, the inner perimeter structure and the outer perimeter structure thereby together forming a single double-walled perimeter structure defining a hollow interior;
a double-walled plate-shaped structure connected to the double-walled structure to be positioned outside of the hollow interior and formed contiguously from the material of the double-walled perimeter, the plate-shaped structure sized and dimensioned to completely occlude the entrance to the appendage while the double-walled perimeter is positioned inside the appendage; and
a plurality of hooks each
affixed to the outer perimeter structure
to extend away from the outer perimeter structure,
forming a barb having a J-shape, and
forming a sharp free end profile at an end of the barb.

2. The device of claim 1, the plurality of hooks defining rows encircling a perimeter of the device.

3. The device of claim 1, hooks of the plurality of hooks having a height of 1.0 mm+/−0.25 mm as measured from a curved end of the J-shape to the sharp free end profile.

4. The device of claim 1, hooks of the plurality of hooks having a length of 1.5 mm+/−0.25 mm as measured from a surface of the outer perimeter structure from which the barb extends to the sharp free end profile of the barb.

5. The device of claim 1, wherein hooks of the plurality of hooks can be pulled straight when the at least one tube is returned to the catheter, and the hook will re-form the J-shape after the at least one tube is again released from the catheter.

6. The device of claim 1, wherein at least two hooks of the plurality of hooks are formed from a single wire bent to form a U-shape before the wire is affixed to the outer perimeter structure.

7. The device of claim 6, wherein a curved portion of the U-shape is folded upon itself when the single wire is affixed to the outer perimeter structure.

8. The device of claim 1, wherein the at least one elongate resilient tube includes first and second elongate resilient tubes, the second elongate resilient tube disposed within the first elongate resilient tube.

9. A method for occluding an appendage inside a living body, comprising delivering by a catheter the device of claim 1, and positioning the device in the appendage to engage the plurality of hooks with body tissue.

10. The method of claim 9, wherein each of the plurality of hooks are sized to pierce the body tissue without passing through an external wall of the appendage.

11. The method of claim 10, wherein the appendage is the left atrial appendage (LAA).

12. The method of claim 9, wherein the at least one elongate resilient tube is a single elongate resilient tube, which is partially involuted to form inner and outer sleeves that form the single double-walled perimeter structure.

13. The device of claim 1, further including a tubular connector having a diameter substantially smaller than the double-walled perimeter structure and the opening of the appendage, the tubular connector extending away from an apex of the double-walled perimeter structure and through the hollow perimeter interior to thereby join the double-walled perimeter structure to the plate-shaped structure.

14. A device for occluding an appendage inside a living body forming an elongate passage and having an open entrance and a hollow interior, comprising:
- at least one elongate resilient tube formed of a mesh of shape memory alloy, the at least one tube compressible to be delivered to the appendage within a catheter, the at least one tube self-expanding as the at least one tube is released from the catheter to contiguously form, sequentially:
- an outer bell-shaped structure
  - that is elongate on a side portion of the bell-shape, the side portion having an external contacting surface sized and dimensioned to flexibly conform to and contact a longitudinal anatomy of an interior surface of the appendage extending along a longitudinal axis of the appendage when the device is deployed within the appendage;
- an inner bell-shaped structure
  - sized and dimensioned along an elongate contact area to flexibly and conformingly abut an interior of the outer bell-shaped structure along the longitudinal axis of the appendage against an opposing surface of the external contacting surface of the outer bell-shaped structure side portion to thereby mutually conform to the interior surface of the appendage together with the outer bell-shaped structure when the device is deployed within the appendage,
  - the inner bell-shaped structure frictionally engaging the outer bell-shaped structure along the elongate contact area to thereby resist displacement of the outer bell-shaped structure along the longitudinal axis of the appendage, the inner bell-shaped structure and the outer bell-shaped structure thereby together forming a single double-walled bell-shaped structure defining a hollow bell interior;

and
- a plurality of hooks each
  - affixed to the outer bell-shaped structure
  - to extend away from the outer bell-shaped structure,
  - forming a barb having J-shape, and
  - forming a sharp free end profile at an end of the barb,
  - having a height extending from the external contacting surface not greater than a depth of the tissue of the longitudinal anatomy of an interior surface of the appendage.

15. The device of claim 14, the plurality of hooks defining rows encircling a perimeter of the device.

16. The device of claim 14, hooks of the plurality of hooks having a height of 1.0 mm+/−0.25 mm as measured from a curved end of the J-shape to the sharp free end profile.

17. The device of claim 14, hooks of the plurality of hooks having a length of 1.5 mm+/−0.25 mm as measured from a surface of the outer perimeter structure from which the barb extends to the sharp free end profile of the barb.

18. The device of claim 14, wherein hooks of the plurality of hooks can be pulled straight when the at least one tube is returned to the catheter, and the hook will re-form the J-shape after the at least one tube is again released from the catheter.

19. The device of claim 14, wherein at least two hooks of the plurality of hooks are formed from a single wire bent to form a U-shape before the wire is affixed to the outer bell-shaped structure.

20. The device of claim 14, wherein a curved portion of the U-shape is folded upon itself when the single wire is affixed to the outer bell-shaped structure.

* * * * *